United States Patent
Krutzik

(10) Patent No.: US 7,141,416 B2
(45) Date of Patent: Nov. 28, 2006

(54) MULTI-PURPOSE OPTICAL ANALYSIS OPTICAL BIO-DISC FOR CONDUCTING ASSAYS AND VARIOUS REPORTING AGENTS FOR USE THEREWITH

(75) Inventor: Siegfried Richard Krutzik, Costa Mesa, CA (US)

(73) Assignee: Burstein Technologies, Inc., Irvine, CA (US)

( * ) Notice: Subject to any disclaimer, the term of this patent is extended or adjusted under 35 U.S.C. 154(b) by 101 days.

(21) Appl. No.: 10/194,396

(22) Filed: Jul. 12, 2002

(65) Prior Publication Data

US 2003/0096434 A1 May 22, 2003

Related U.S. Application Data

(60) Provisional application No. 60/391,792, filed on Jun. 26, 2002, provisional application No. 60/390,238, filed on Jun. 20, 2002, provisional application No. 60/353,745, filed on Jan. 30, 2002, provisional application No. 60/353,770, filed on Jan. 30, 2002, provisional application No. 60/353,741, filed on Jan. 30, 2002, provisional application No. 60/304,855, filed on Jul. 12, 2001.

(51) Int. Cl.
*C12M 1/34* (2006.01)
*C12M 3/00* (2006.01)

(52) U.S. Cl. .................. 435/288.5; 422/57; 422/58; 422/64; 422/68.1; 435/7.1; 435/287.1; 435/287.9; 435/288.4

(58) Field of Classification Search .................. 422/50, 422/55, 57–58, 64, 68.1, 82.05, 82.09, 72; 435/4, 7.1, 7.4–7.92, 287.1, 287.9, 288.7, 435/6, 287.2, 288.4, 288.5; 436/63, 164, 436/501, 45, 518, 524, 525, 43

See application file for complete search history.

(56) References Cited

U.S. PATENT DOCUMENTS 4,366,241 A 12/1982 Tom et al.

(Continued)

FOREIGN PATENT DOCUMENTS

CN 1208464 2/1999

(Continued)

OTHER PUBLICATIONS

Duffy et al. "Microfabricated Centrifugal Microfluidic Systems: Characterization and Multiple Enzymatic Assays". Analytical Chemistry 1999, 71(20):4669-4678.*

(Continued)

*Primary Examiner*—Long V. Le
*Assistant Examiner*—Leon Y. Lum
(74) *Attorney, Agent, or Firm*—Knobbe, Martens, Olson & Bear, LLP

(57) ABSTRACT

The present invention relates to optical bio-disc systems and related methods and to immobilizing receptor molecules. When a sample is injected into a fluidic circuit, the target agent binds to a capture probe bound in a capture zone. A signal is generated from tags attached to a reporter probe that has specific affinity to the target agent. The assays and methods of the present invention are implemented on an optical bio-disc. The optical bio-disc includes a flow channel having capture zones and in fluid communications with a mixing chamber, and a peripheral waste reservoir. The optical bio-disc is implemented on an optical bio-disc that has information encoding format such as CD. An disc drive assembly is employed to rotate the optical bio-disc, read and process any encoded information, and analyze the samples in the flow channel of the optical bio-disc.

18 Claims, 24 Drawing Sheets

U.S. PATENT DOCUMENTS

| | | | |
|---|---|---|---|
| 4,687,638 A * | 8/1987 | Benajam | 422/73 |
| 5,061,381 A * | 10/1991 | Burd | 210/789 |
| 5,122,284 A * | 6/1992 | Braynin et al. | 210/782 |
| 5,132,097 A | 7/1992 | Van Deusen et al. | |
| 5,145,784 A | 9/1992 | Cox et al. | |
| 5,173,262 A * | 12/1992 | Burtis et al. | 422/72 |
| 5,329,461 A * | 7/1994 | Allen et al. | 702/26 |
| 5,334,837 A | 8/1994 | Ikeda et al. | |
| 5,413,939 A | 5/1995 | Gustafson et al. | |
| 5,453,969 A | 9/1995 | Psaltis et al. | |
| 5,462,839 A | 10/1995 | de Rooij et al. | |
| 5,471,455 A | 11/1995 | Jabr | |
| 5,472,603 A * | 12/1995 | Schembri | 210/380.1 |
| 5,478,527 A * | 12/1995 | Gustafson et al. | 422/82.11 |
| 5,488,567 A | 1/1996 | Allen et al. | |
| 5,497,367 A | 3/1996 | Yamagami et al. | |
| 5,518,930 A | 5/1996 | Burd | |
| 5,536,548 A | 7/1996 | Koji et al. | |
| 5,591,643 A * | 1/1997 | Schembri | 436/45 |
| 5,618,926 A | 4/1997 | Salamone et al. | |
| 5,755,942 A | 5/1998 | Zanzucchi et al. | |
| 5,763,262 A * | 6/1998 | Wong et al. | 435/287.2 |
| 5,789,167 A | 8/1998 | Konrad | |
| 5,858,804 A | 1/1999 | Zanzucchi et al. | |
| 5,863,708 A | 1/1999 | Zanzucchi et al. | |
| 5,872,723 A * | 2/1999 | DeCusatis et al. | 700/306 |
| 5,882,903 A * | 3/1999 | Andrevski et al. | 435/91.2 |
| 5,892,577 A * | 4/1999 | Gordon | 356/73 |
| 5,922,617 A | 7/1999 | Wang et al. | |
| 5,935,785 A | 8/1999 | Reber et al. | |
| 6,004,617 A | 12/1999 | Schultz et al. | |
| 6,013,513 A | 1/2000 | Reber et al. | |
| 6,030,581 A * | 2/2000 | Virtanen | 422/68.1 |
| 6,063,589 A * | 5/2000 | Kellogg et al. | 435/24 |
| 6,117,630 A | 9/2000 | Reber et al. | |
| 6,137,897 A | 10/2000 | Emi et al. | |
| 6,143,247 A * | 11/2000 | Sheppard et al. | 422/63 |
| 6,143,248 A * | 11/2000 | Kellogg et al. | 422/72 |
| 6,299,839 B1 * | 10/2001 | Karunaratne et al. | 422/63 |
| 6,319,469 B1 * | 11/2001 | Mian et al. | 422/64 |
| 6,342,349 B1 | 1/2002 | Virtanen | |
| 6,372,425 B1 | 4/2002 | Arnold et al. | |
| 6,395,562 B1 | 5/2002 | Hammock et al. | |
| 6,649,351 B1 | 11/2003 | Matray et al. | |
| 6,776,965 B1 * | 8/2004 | Wyzgol et al. | 422/100 |
| 6,821,788 B1 * | 11/2004 | Cesarczyk | 436/165 |
| 2001/0055812 A1 | 12/2001 | Mian et a. | |
| 2002/0106786 A1 | 8/2002 | Carvalho et al. | |
| 2002/0117659 A1 | 8/2002 | Lieber et al. | |
| 2003/0003464 A1 | 1/2003 | Phan et al. | |

FOREIGN PATENT DOCUMENTS

| | | |
|---|---|---|
| CN | 1285916 A | 2/2001 |
| EP | 0 392 475 A2 | 10/1990 |
| EP | 0 417 305 A1 | 3/1991 |
| EP | 0 504 432 A1 | 9/1992 |
| EP | 0 521 421 A2 | 1/1993 |
| EP | 0 693 560 A2 | 1/1996 |
| EP | 0 703 825 B1 | 4/1996 |
| GB | 2 337 113 A | 11/1999 |
| GB | 2 337 113 B | 11/1999 |
| WO | WO 93/22053 | 11/1993 |
| WO | WO 95/34890 | 12/1995 |
| WO | WO 96/09548 | 3/1996 |
| WO | WO 97/21090 | 6/1997 |
| WO | WO 97/41256 | 11/1997 |
| WO | WO 98/07019 * | 2/1998 |
| WO | WO 98/28623 | 7/1998 |
| WO | WO 98/38510 | 9/1998 |
| WO | WO 98/53311 | 11/1998 |
| WO | WO 99/32663 | 7/1999 |
| WO | WO 99/35499 | 7/1999 |
| WO | WO 00/05582 | 2/2000 |
| WO | WO 00/78455 A1 | 12/2000 |
| WO | WO 02/42498 A2 | 5/2002 |

OTHER PUBLICATIONS

Patel et al., "Immobilization of protein molecules onto homogenous and mixed carboxylate-terminated self-assembled monolayers." Langmuir (1997), 13:6485-6490.

Tibbe et al., "Cell Analysis System Based on Immunomagnetic Cell Selection and Alignment Followed by Immunofluorescent Analysis Using Compact Disk Technologies", Cytometry 43, pp. 31-37 (2001).

Vossmeyer et al., "Light-Directed Assembly of Nanoparticles", Angew. Chem. Int. Ed. Engl. 1997, 36, No. 10, pp. 1080-1083.

US 6,200,755, 03/2001, Virtanen (withdrawn)

* cited by examiner

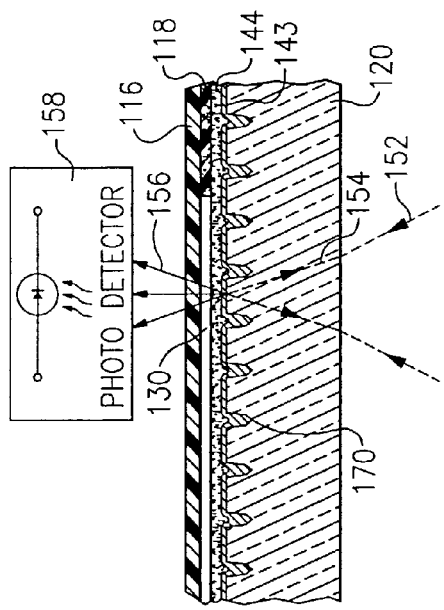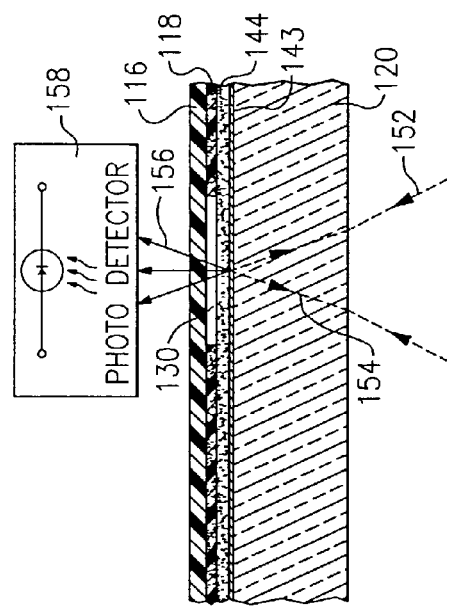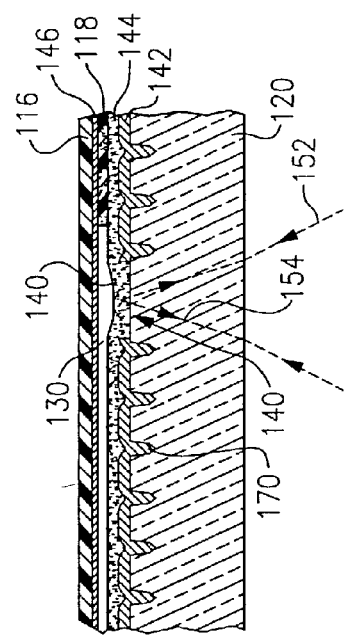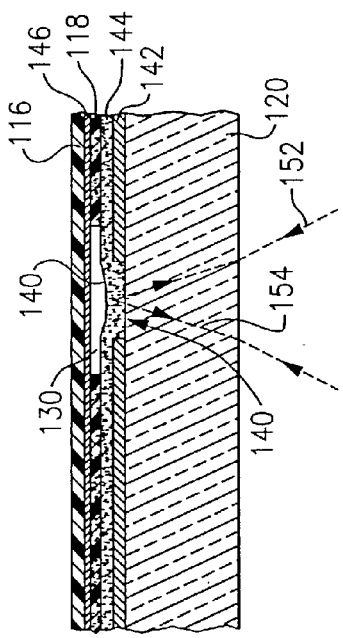

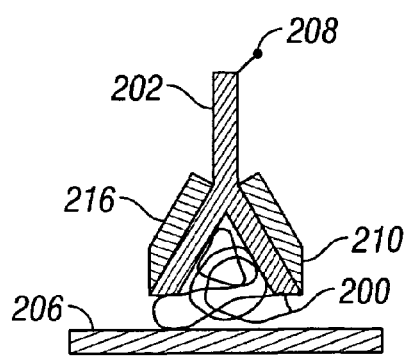
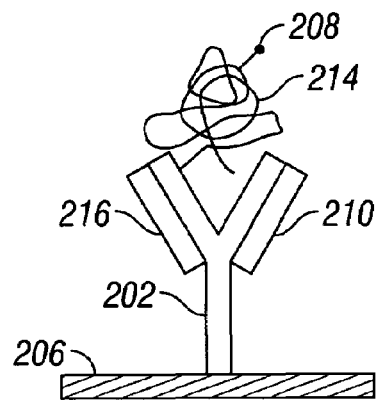
FIG. 23A  FIG. 23B
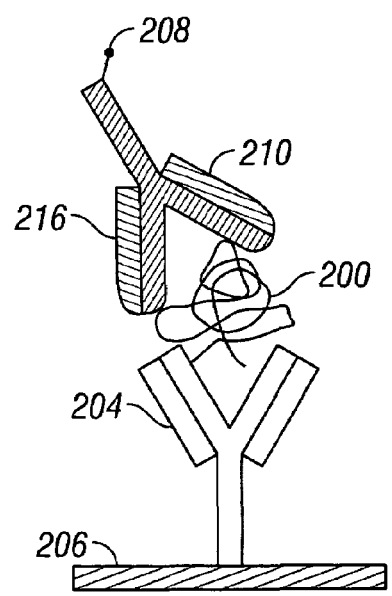
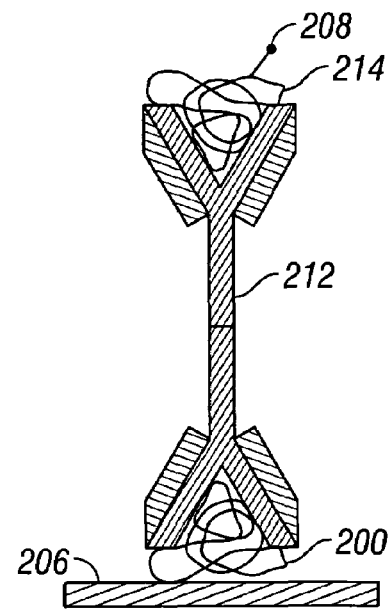
FIG. 23C  FIG. 23D

MULTI-PURPOSE OPTICAL ANALYSIS OPTICAL BIO-DISC FOR CONDUCTING ASSAYS AND VARIOUS REPORTING AGENTS FOR USE THEREWITH

CROSS-REFERENCE TO RELATED APPLICATIONS

The present application claims the benefit of priority from U.S. Provisional Patent Applications Ser. No. 60/304,855 filed on Jul. 12, 2001; Ser. No. 60/353,741 filed on Jan. 30, 2002; Ser. No. 60/353,770 filed on Jan. 30, 2002; Ser. No. 60/353,745 filed on Jan. 30, 2002; Ser. No. 60/390,238 filed on Jun. 20, 2002; and Ser. No. 60/391,792 filed on Jun. 26, 2002. All of which are herein incorporated by reference in their entireties.

BACKGROUND OF THE INVENTION

1. Field of Invention

The present invention relates to methods and design of optical bio-discs for the detection, and for quantitative and qualitative analysis of bindable substances. More specifically, this invention is directed to methods and apparatus for detection and quantification of bindable substances through affinity reaction with a solid phase linked binding substance. The solid phase is preferably provided by the surface of an optical bio-disc, which carries the immobilized binding reagent and encoded information for performing the analysis. The analyte of interest is carried within fluidic circuits of the optical bio-disc. Separation of bound analyte from free analytes may be performed using centrifugal force imparted by rotating the optical bio-disc.

2. Optical Bio-Discussion of the Related Art

The detection and quantification of analytes in the blood or other body fluids are essential for diagnosis of diseases, elucidation of the pathogenesis, and for monitoring the response to drug treatment. Traditionally, diagnostic assays are performed in laboratories by trained technicians using complex apparatus. Performing these assays is usually time-consuming and costly. Thus, there is a significant need to make diagnostic assays and forensic assays of all types faster and more local to the end-user. Ideally, clinicians, patients, investigators, the military, other health care personnel, and consumers should be able to test themselves for the presence of certain risk factors or disease indicators in their systems, and to test for the presence of certain biological material at a crime scene or on a battlefield. At present, there are a number of medical diagnostic, silicon-based, devices with nucleic acids and/or proteins attached thereto that are commercially available or under development. These chips are not for use by the end-user, or for use by persons or entities lacking very specialized expertise and expensive equipment.

Commonly assigned U.S. Pat. No. 6,030,581 entitled "Laboratory in a Disk" issued Feb. 29, 2000 (the '581 patent) is hereby incorporated by reference in its entirety. The '581 patent optical bio-discloses an apparatus that includes an optical bio-disc, adapted to be read by an optical reader, which has a sector having a substantially self-contained assay system useful for localizing and detecting an analyte suspected of being in a sample.

SUMMARY OF THE INVENTION

Analysis of biological fluids aimed at the quantitative and qualitative determination of substances associated with a wide variety of physiological disorders, bioresearch, proteomics, environmental studies, agriculture, and food industry, relies on specific binding assays from which the immunoassay plays a dominant role. The outstanding specificity and sensitivity for quantitative determination of an almost limitless number of analytes in practically any milieu, and the ability to miniaturize and adapt to automation makes them ideal tools for routine assays.

Antibody binding techniques are based on the interaction of a binding antibody, receptor, or other binding proteins with an antigen or a specific ligand molecule and the formation of an antibody-antigen or receptor-ligand complex. By changing certain conditions a binding assay can be designed to determine either an analyte, ligand, or target binding reagent or an antibody of interest. The steps are similar but the assay configuration provides results pertinent to the antigen or antibody of interest.

Capture Probe Binding and Sample Application

When the sample is injected into a micro-channel, fluidic circuit, or flow channel on an optical bio-disc, the target agent including, for example, target antigen or antibody, binds to a capture probe bound in a capture or target zone on a solid support such as an optical bio-disc substrate. The capture probe may be an antigen recognized by the target antibody or an antibody or receptor with specific affinity to the target antigen or ligand. Following the binding step, unbound target agent is removed through a wash step. It should be understood that various techniques, procedures and chemistries, know in the art, may be used to bind the capture probe onto a solid support including, but not limited to, direct covalent binding of probes onto a metallic or activated surface, passive adsorption, and through cross-linking reagents.

Further details relating to surface chemistries used to bind probes onto solid support are optical bio-disclosed in, for example, the above incorporated commonly assigned co-pending U.S. Provisional Application Ser. No. 60/353,770 entitled "Capture Layer Assemblies Including Metal Layer for Immobilization of Receptor Molecules and Related Optical Assay Optical bio-discs" filed Jan. 30, 2002; and U.S. Provisional Application Ser. No. 60/353,745 entitled "Capture Layer Assemblies Including Polymer Substrates for Immobilization of Receptor Molecules and Related Optical Assay Optical bio-discs" filed Jan. 30, 2002.

In addition to surface chemistries for attaching capture probes, blocking agents may be used to block areas within the capture or target zone and the flow channel where capture probes are not bound (non-capture areas) to prevent non-specific binding of the target or analyte, signal probes, and reporters onto these areas. Blocking agents include, but are not limited to proteins such as BSA, gelatin, sugars such as sucrose, detergents such as tween-20, genetic material such as sheared salmon sperm DNA, and polyvinyl alcohol.

Signal Generation

Signal is generated from tags or labels attached to a signal or reporter agents or probes that has specific affinity to the target agent. Signal agents or probes may include, for example, signal antibodies or signal ligands, tagged with microspheres, sub-micron nanospheres, or enzymes. The microspheres or nanospheres may be fluorescent labeled (fluospheres), phosphorescent, luminecent, or chemiluminescent. The microspheres or nanospheres may also carry different chemical functionalities including, for example, carboxyl, amino, aldehyde, and hydrazine functional groups. These functional groups may facilitate binding of the signal agent. The enzyme may facilitate a chemical reaction that produces fluorescence, color, or a detectable signal in the presence of a suitable substrate. For example, conjugated horseradish peroxidase (HRP; Pierce, Rockford, Ill.) may be used with the substrate 3,3,5,5-tetramethylbenzidine (TMB; Calbiochem cat. no. 613548, CAS-54827-17-7) in the presence of hydrogen peroxide to produce an insoluble precipitate. Horseradish peroxidase can also be used in conjunction with CN/DAB (4-chloronaphthol/3,3'-diaminobenzidine, tetrahydrochloride), 4-CN (4-chloro-1-napthol), AEC (3-amino-9-ethyl carbazol) and DAB (3,3-diaminobenzidine tetrahydrochloride) to form insoluble precipitates. Similarly, the enzyme alkaline phosphatase (AP) can be used with the substrate bromochloroindolylphosphate in the practice of the present invention. Other suitable enzyme/substrate combinations will be apparent to those of skill in the art.

Detection

The signal from the microspheres or the enzyme reaction can be read with the optical bio-disc readers developed to be utilized in conjunction herewith. Either a bottom detector on an optical bio-disc with a reflective cover, or a top detector with a transmissive optical bio-disc may be employed as the optical bio-disc reader for the assay and optical bio-disc inventions optical bio-disclosed herein.

Optical Bio-Disc Implementation

The assays and methods of the present invention may be advantageously implemented on an analysis optical bio-disc, modified optical bio-disc, or optical bio-disc. The optical bio-disc may include a flow channel having target or capture zone, a return channel in fluid communication therewith, and in some embodiments a mixing chamber in fluid communication with the flow channel.

In one embodiment, at least one caption agent is bound to an active layer such that the capture agent is immobilized on the active layer with a target zone to thereby form a capture zone. The active layer is formulated to immobilize a pellet formed by an enzyme reaction.

The optical bio-disc may be implemented on an optical bio-disc including an information encoding format such as CD, CD-R, or DVD or a modified version thereof. The optical bio-disc may include encoded information for performing, controlling, and post-processing the test or assay. For example, such encoded information may be directed to controlling the rotation rate of the optical bio-disc, incubation time, incubation temperature, and/or specific steps of the assay. Depending on the test, assay, or investigational protocol, the rotation rate may be variable with intervening or consecutive sessions of acceleration, constant speed, and deceleration. These sessions may be closely controlled both as to speed and time of rotation to provide, for example, mixing, agitation, or separation of fluids and suspensions with agents, reagents, DNA, RNA, antigen, antibodies, ligands, and receptors.

Drive Implementation

An disc drive assembly or reader may be employed to rotate the optical bio-disc, read and process any encoded information stored on the optical bio-disc, and analyze the samples in the flow channel of the optical bio-disc. The disc drive is thus provided with a motor for rotating the optical bio-disc, a controller for controlling the rate of rotation of the optical bio-disc, a processor for processing return signals from the optical bio-disc, and an analyzer for analyzing the processed signals. The drive may include software specifically developed for performing the assays optical bio-disclosed herein.

The rotation rate of the motor is controlled to achieve the desired rotation of the optical bio-disc. The disc drive assembly may also be utilized to write information to the optical bio-disc either before or after the test material in the flow channel and target or capture zone is interrogated by the read beam of the drive and analyzed by the analyzer. The optical bio-disc may include encoded information for controlling the rotation rate of the optical bio-disc, providing processing information specific to the type of test to be conducted, and for displaying the results on a display monitor associated with the bio-drive in accordance with the assay methods relating hereto.

Other Implementations of the Current Invention

The present invention may be readily implemented in some of the optical bio-discs, assays, and systems optical bio-disclosed in the following commonly assigned and co-pending patent applications: U.S. patent application Ser. No. 09/378,878 entitled "Methods and Apparatus for Analyzing Operational and Non-operational Data Acquired from Optical bio-discs" filed Aug. 23, 1999; U.S. Provisional Patent Application Ser. No. 60/150,288 entitled "Methods and Apparatus for Optical bio-disc Data Acquisition Using Physical Synchronization Markers" filed Aug. 23, 1999; U.S. patent application Ser. No. 09/421,870 entitled "Trackable Optical bio-discs with Concurrently Readable Analyte Material" filed Oct. 26, 1999; U.S. patent application Ser. No. 09/643,106 entitled "Methods and Apparatus for Optical bio-disc Data Acquisition Using Physical Synchronization Markers" filed Aug. 21, 2000; U.S. patent application Ser. No. 09/999,274 entitled "Optical bio-discs with Reflective Layers" filed on Nov. 15, 2001; U.S. patent application Ser. No. 09/988,728 entitled "Methods And Apparatus For Detecting And Quantifying Lymphocytes With Optical bio-discs" filed on Nov. 20, 2001; U.S. patent application Ser. No. 09/988,850 entitled "Methods and Apparatus for Blood Typing with Optical bio-discs" filed on Nov. 19, 2001; U.S. patent application Ser. No. 09/989,684 entitled "Apparatus and Methods for Separating Agglutinants and Disperse Particles" filed Nov. 20, 2001; U.S. patent application Ser. No. 09/997,741 entitled "Dual Bead Assays Including Optical bio-discs and Methods Relating Thereto" filed Nov. 27, 2001; U.S. patent application Ser. No. 09/997,895 entitled "Apparatus and Methods for Separating Components of Particulate Suspension" filed Nov. 30, 2001; U.S. patent application Ser. No. 10/005,313 entitled "Optical bio-discs for Measuring Analytes" filed Dec. 7, 2001; U.S. patent application Ser. No. 10/006,371 entitled "Methods for Detecting Analytes Using Optical bio-discs and Optical bio-disc Readers" filed Dec. 10, 2001; U.S. patent application Ser. No. 10/006,620 entitled "Multiple Data Layer Optical bio-discs for Detecting Analytes" filed Dec. 10, 2001; U.S. patent application Ser. No. 10/006,619 entitled "Optical bio-disc Assemblies for Performing Assays" filed Dec. 10, 2001; U.S. patent application Ser. No. 10/020,140 entitled "Detection System For Disk-Based Laboratory And Improved Optical bio-disc Including Same" filed Dec. 14, 2001; U.S. patent application Ser. No. 10/035,836 entitled "Surface Assembly For Immobilizing DNA Capture Probes And Bead-Based Assay Including Optical bio-discs And Methods Relating Thereto" filed Dec. 21, 2001; U.S. patent application Ser. No. 10/038,297 entitled "Dual Bead Assays Including Covalent Linkages For Improved Specificity And Related Optical Analysis Optical bio-discs" filed Jan. 4, 2002; U.S. patent application Ser. No. 10/043,688 entitled "Optical bio-disc Analysis System Including Related Methods For Biological and Medical Imaging" filed Jan. 10, 2002; U.S. Provisional Application Ser. No. 60/363,949, entitled "Methods for Differential Cell Counts Including Leukocytes and Use of Optical bio-disc for Performing Same" filed Mar. 12, 2002; U.S. patent application Ser. No. 10/150,702 entitled "Surface Assembly For Immobilizing DNA Capture Probes In Genetic Assays Using Enzymatic Reactions To Generate Signal In Optical bio-discs And Methods Relating Thereto" filed May 17, 2002; and U.S. Provisional Application Ser. No. 60/388,132, entitled "Biomagnetic Assays and Related Optical bio-disc Systems" filed Jun. 12, 2002. All of these applications are herein incorporated by reference. They thus provide background and related optical bio-disclosure as support hereof as if fully repeated herein.

BRIEF DESCRIPTION OF THE DRAWING FIGURES

Further objects of the present invention together with additional features contributing thereto and advantages accruing therefrom will be apparent from the following description of the preferred embodiments of the invention which are shown in the accompanying drawing figures with like reference numerals indicating like components throughout, wherein.

Figure 1:
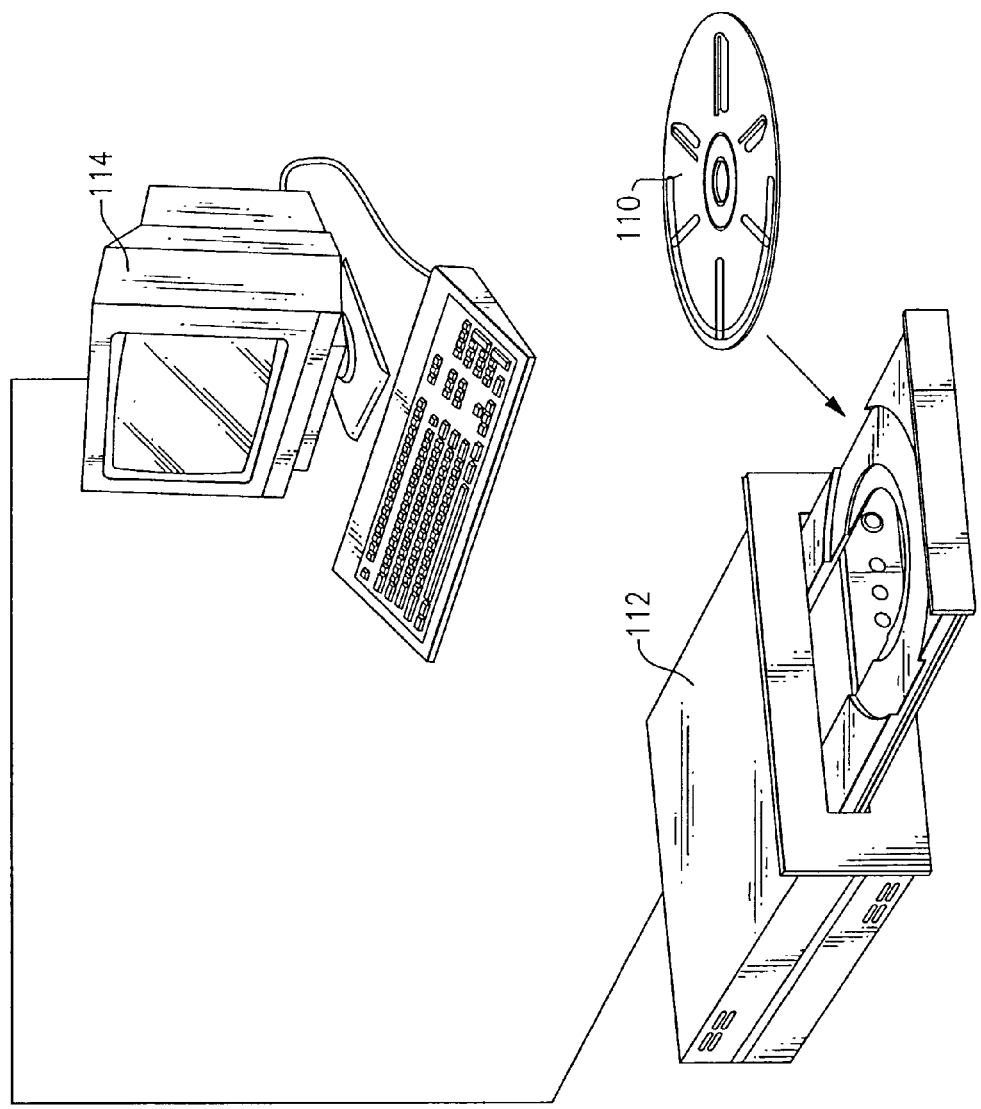
FIG. 1 is a pictorial representation of an optical bio-disc system according to the present invention.
Figure 2:
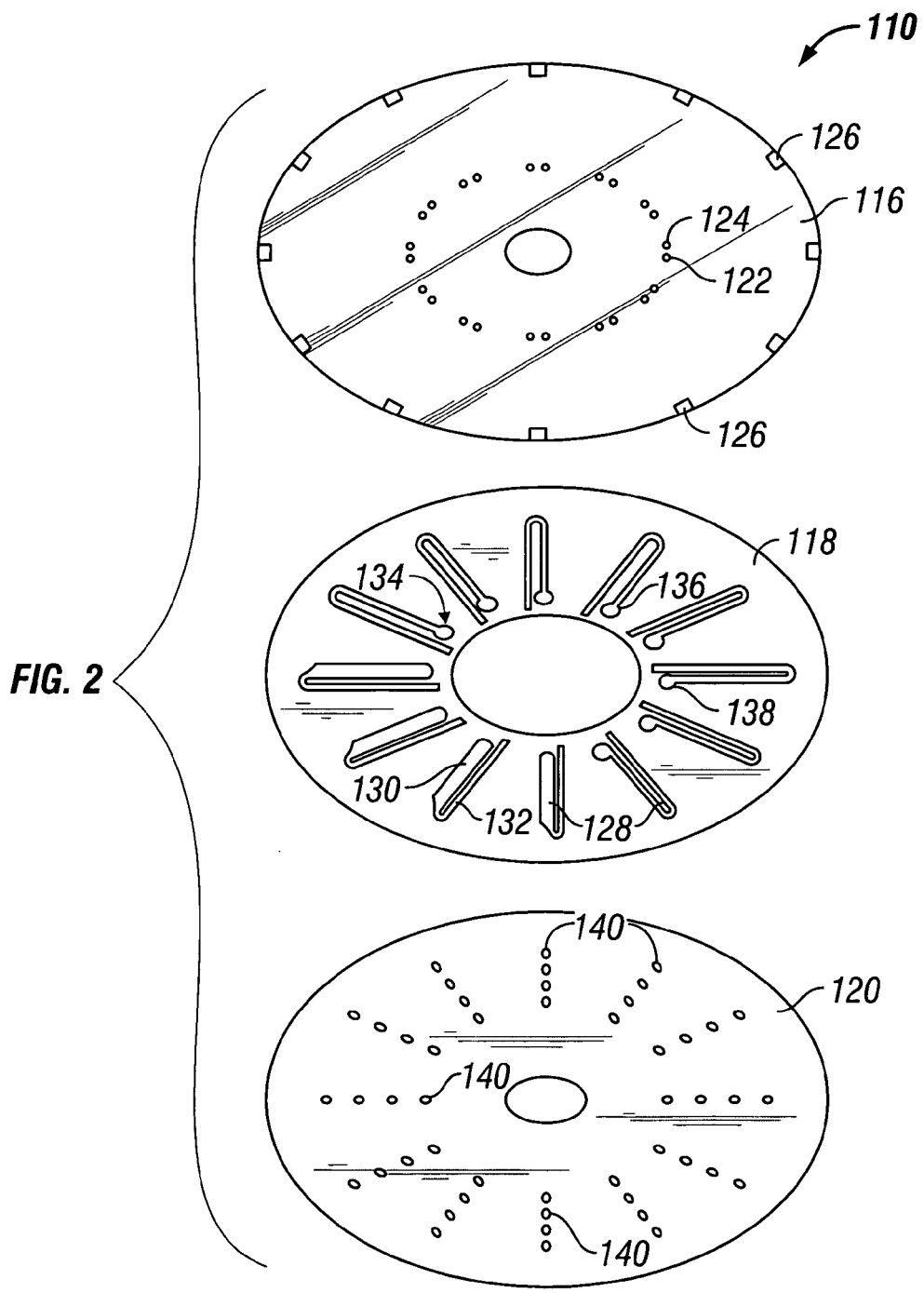
FIG. 2 is an exploded perspective view of a reflective optical bio-disc as utilized in conjunction with the present invention.
Figure 3:
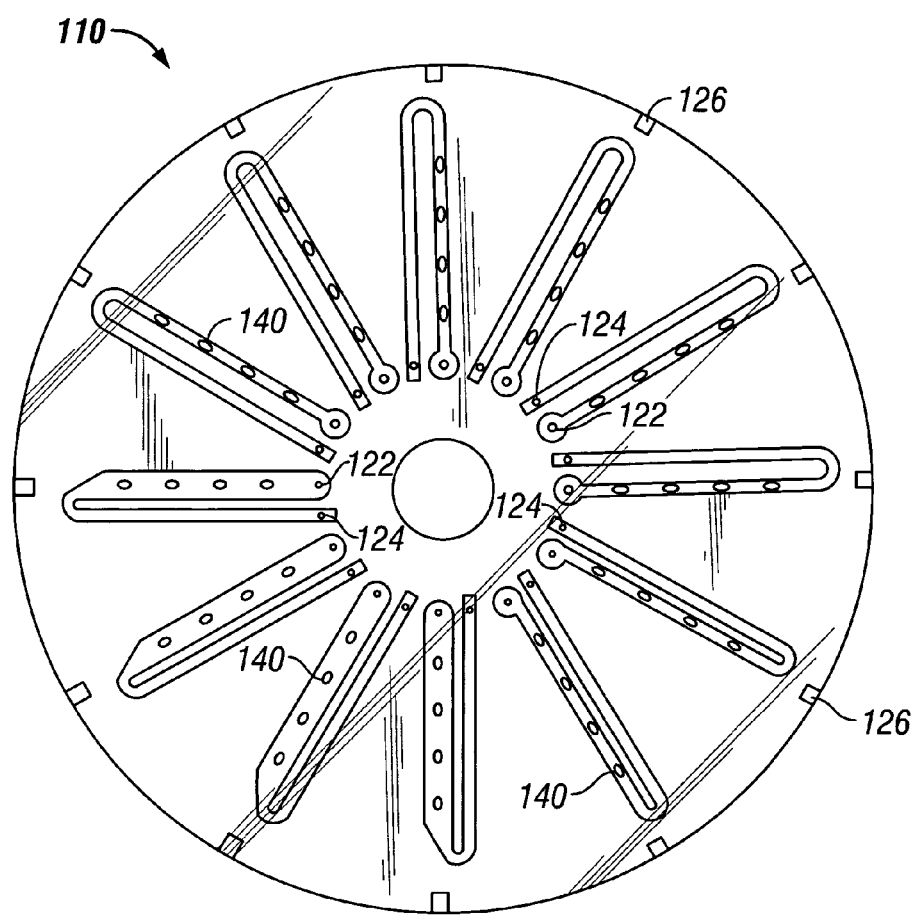
FIG. 3 is a top plan view of the optical bio-disc shown in FIG. 2.
Figure 4:
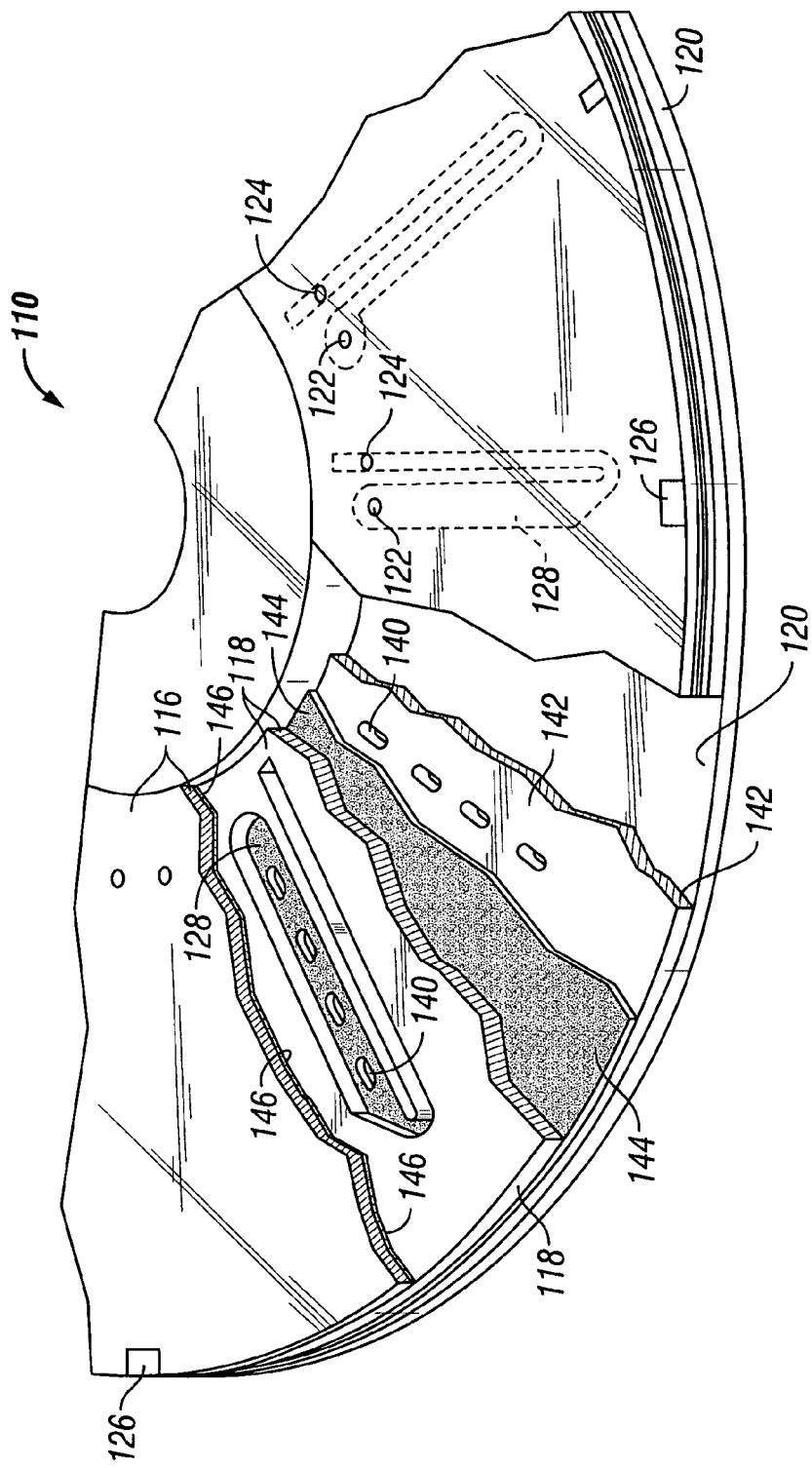
FIG. 4 is a perspective view of the optical bio-disc illustrated in FIG. 2 with cut-away sections showing the different layers of the optical bio-disc.
Figure 5:
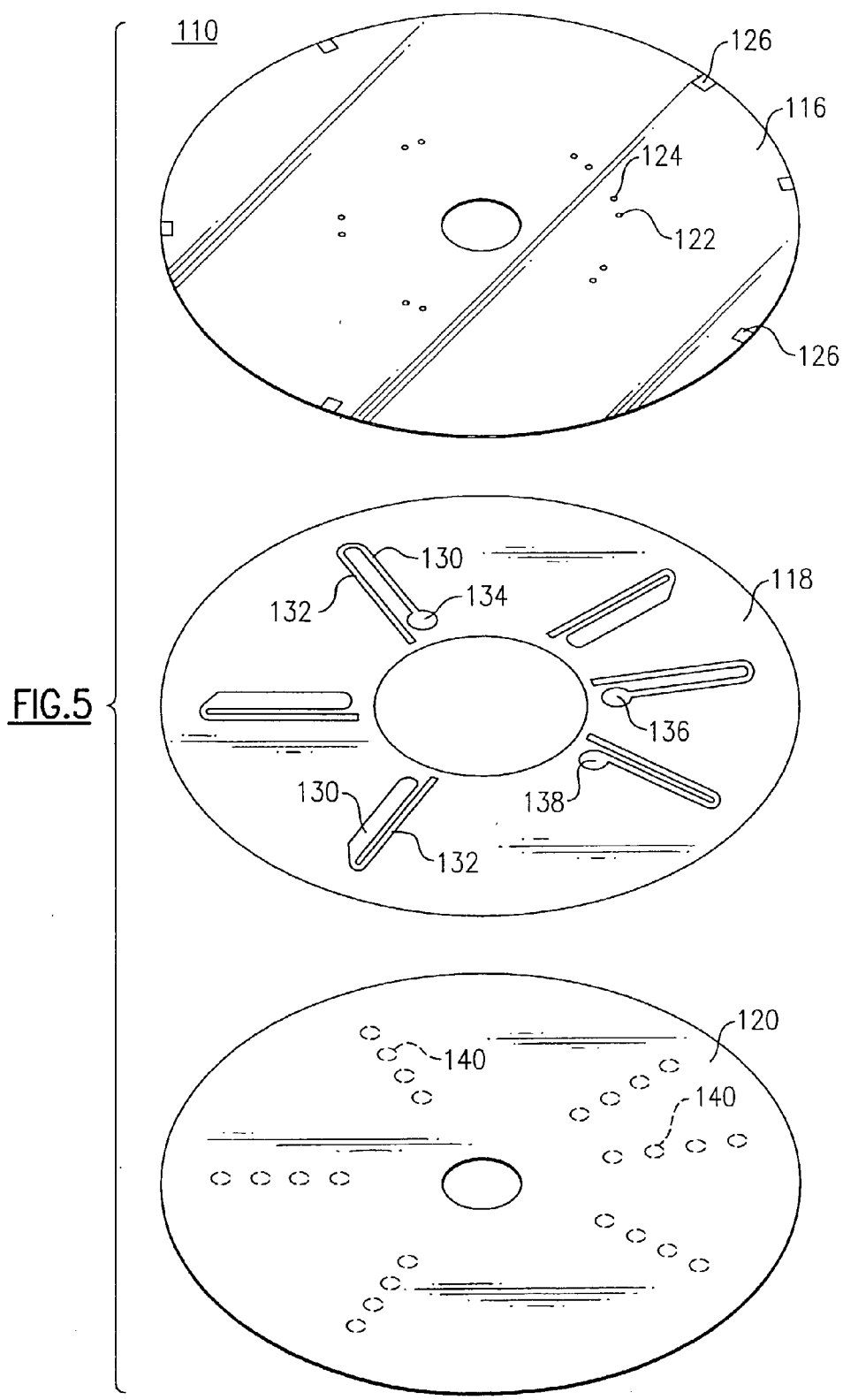
FIG. 5 is an exploded perspective view of a transmissive optical bio-disc as employed in conjunction with the present invention.
Figure 6:
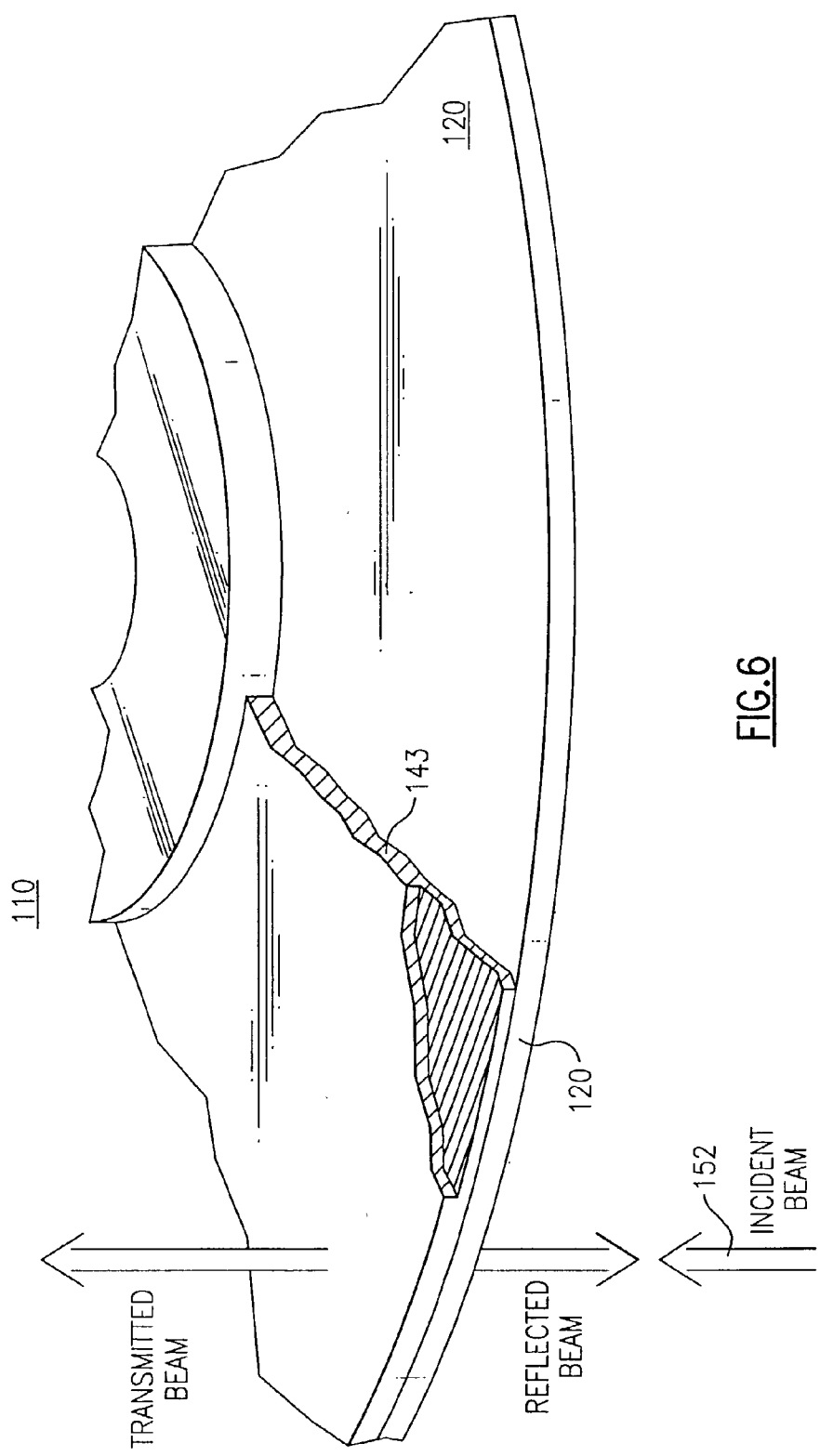
FIG. 6 is a perspective view representing the optical bio-disc shown in FIG. 5 with a cut-away section illustrating the functional aspects of a semi-reflective layer of the optical bio-disc.
Figure 8:
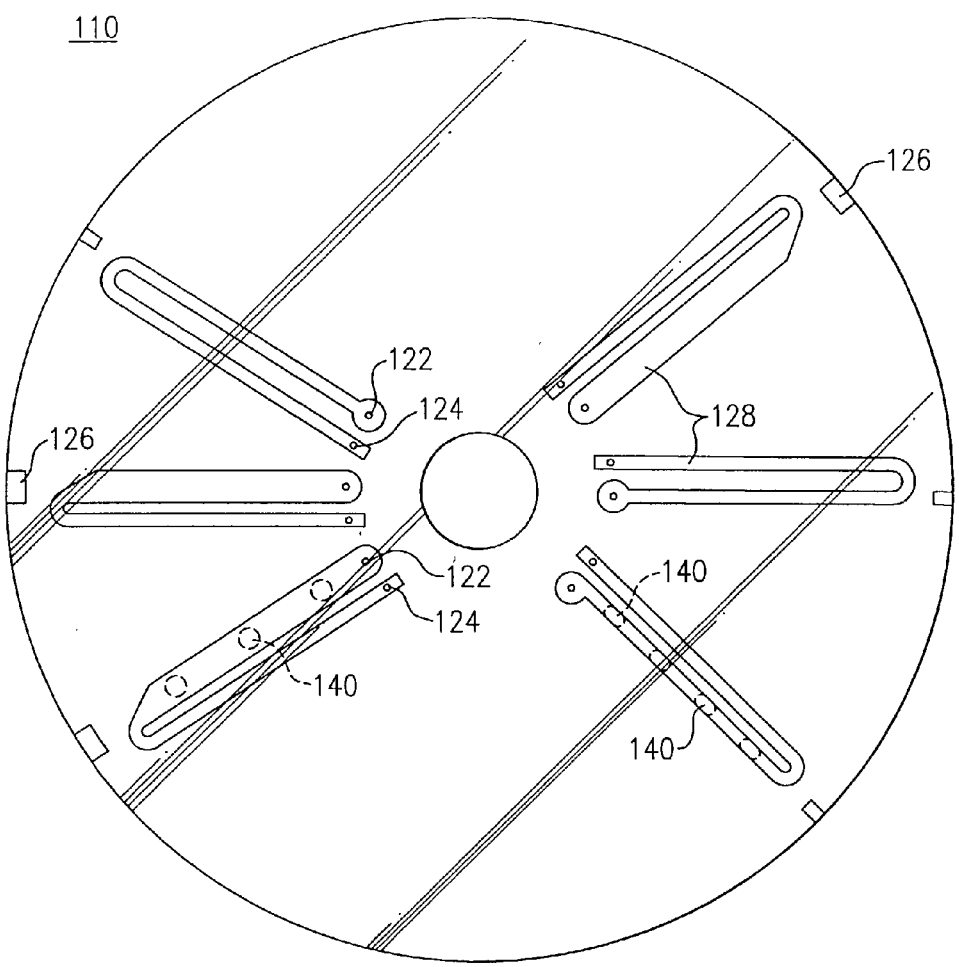
FIG. 8 is a top plan view of the optical bio-disc shown in FIG. 5.
Figure 9:
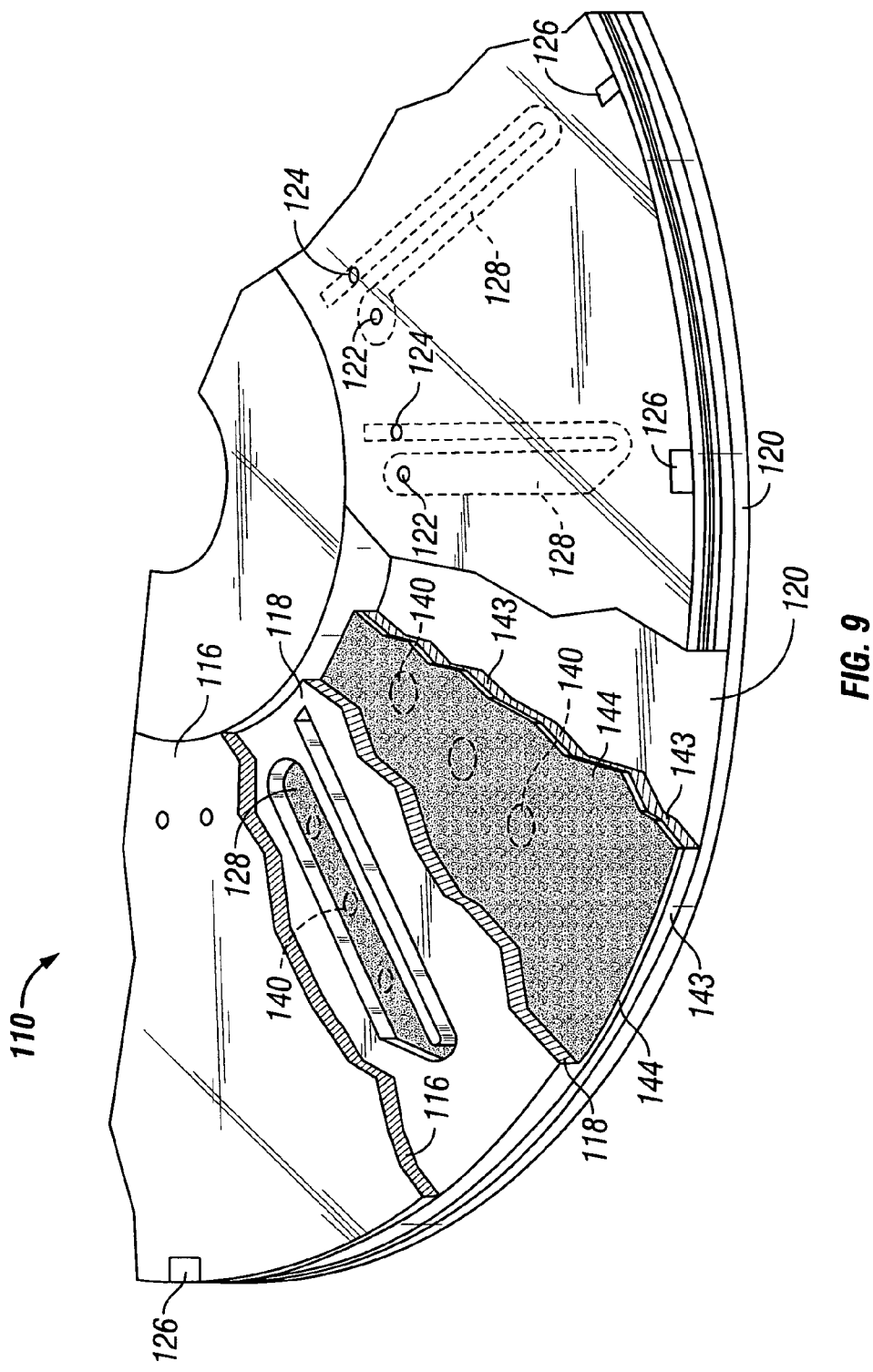
FIG. 9 is a perspective view of the optical bio-disc illustrated in FIG. 5 with cut-away sections showing the different layers of the optical bio-disc including the type of semi-reflective layer shown in FIG. 6.
Figure 11A:
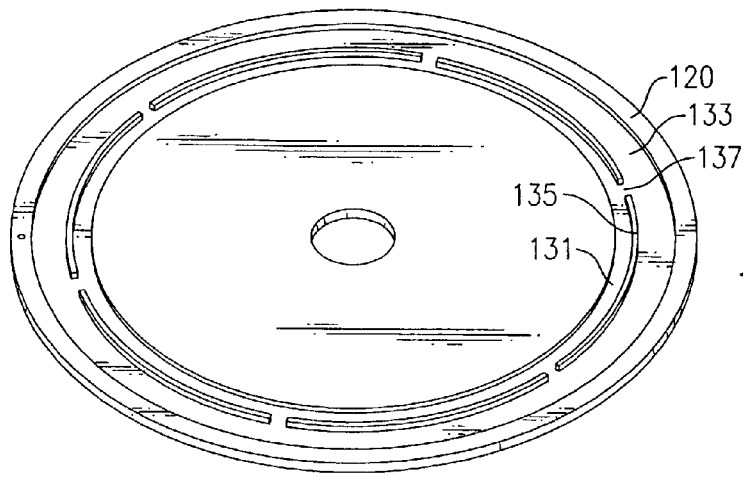
Figure 11B:
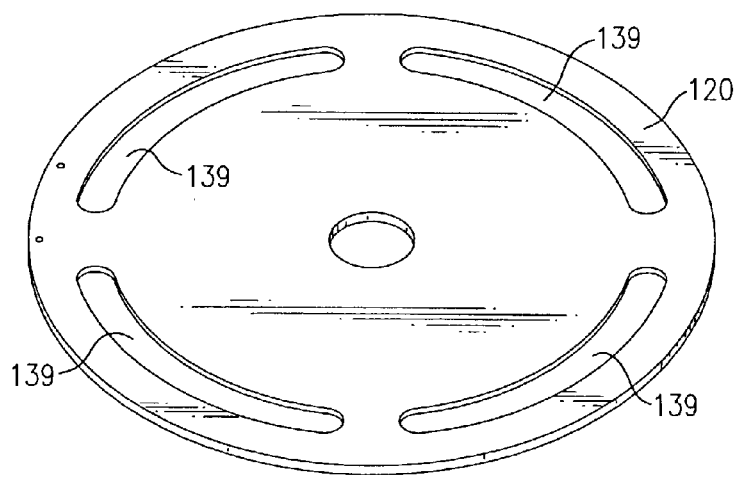
Figure 11C:
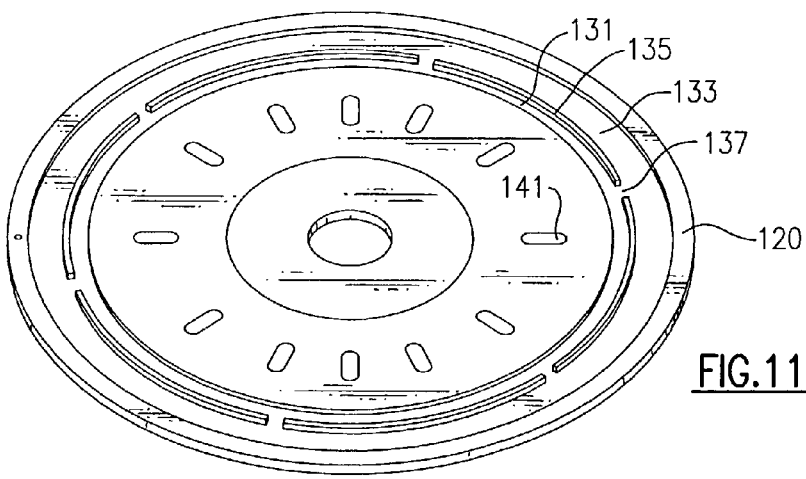
Figure 12:
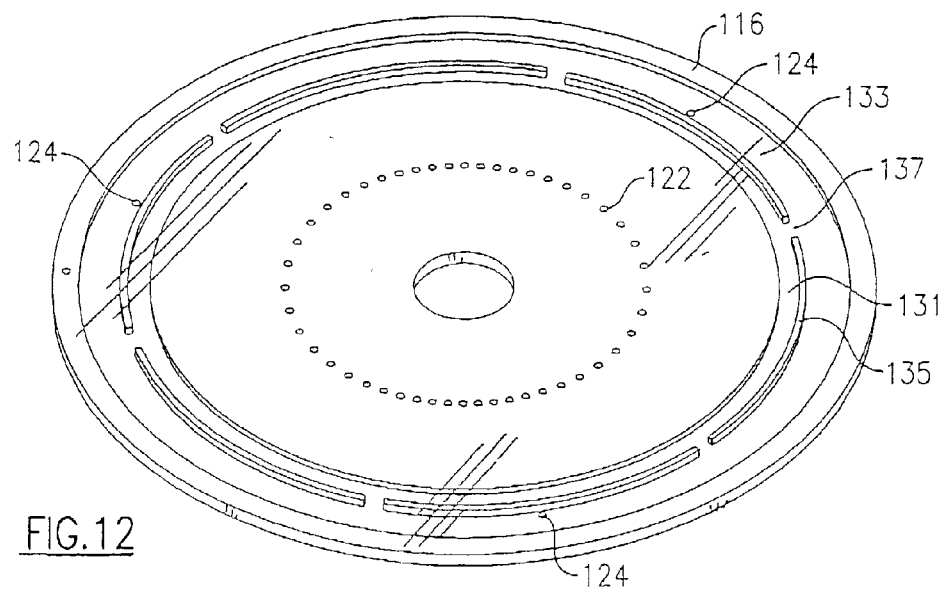
Figure 13:
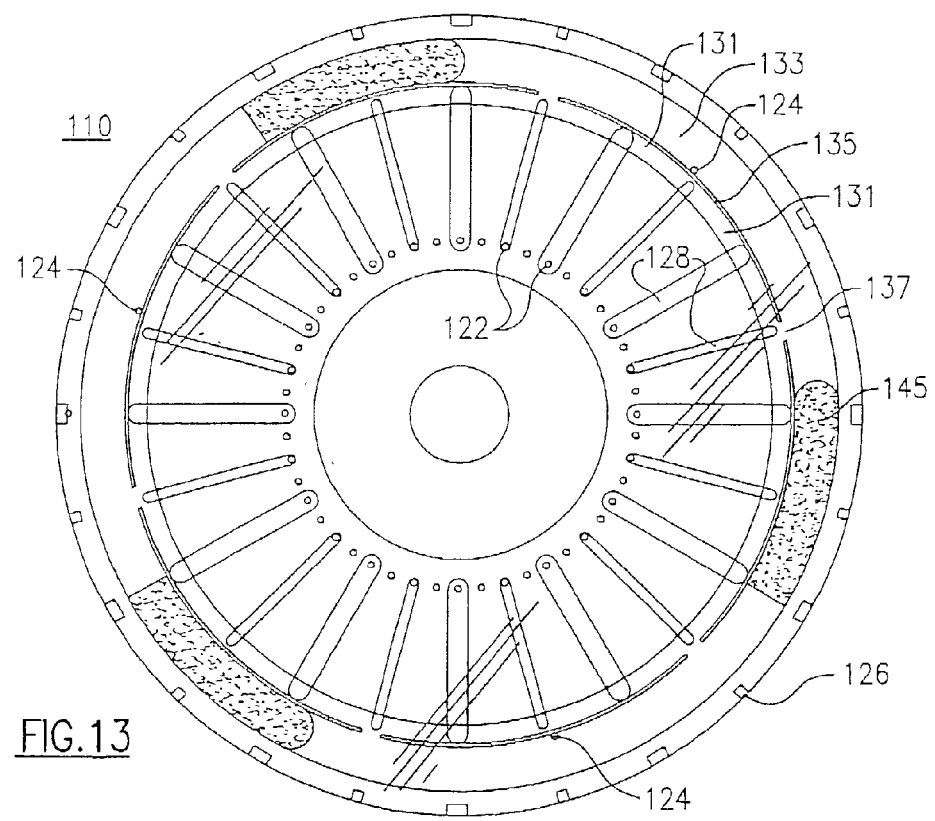
Figure 14:
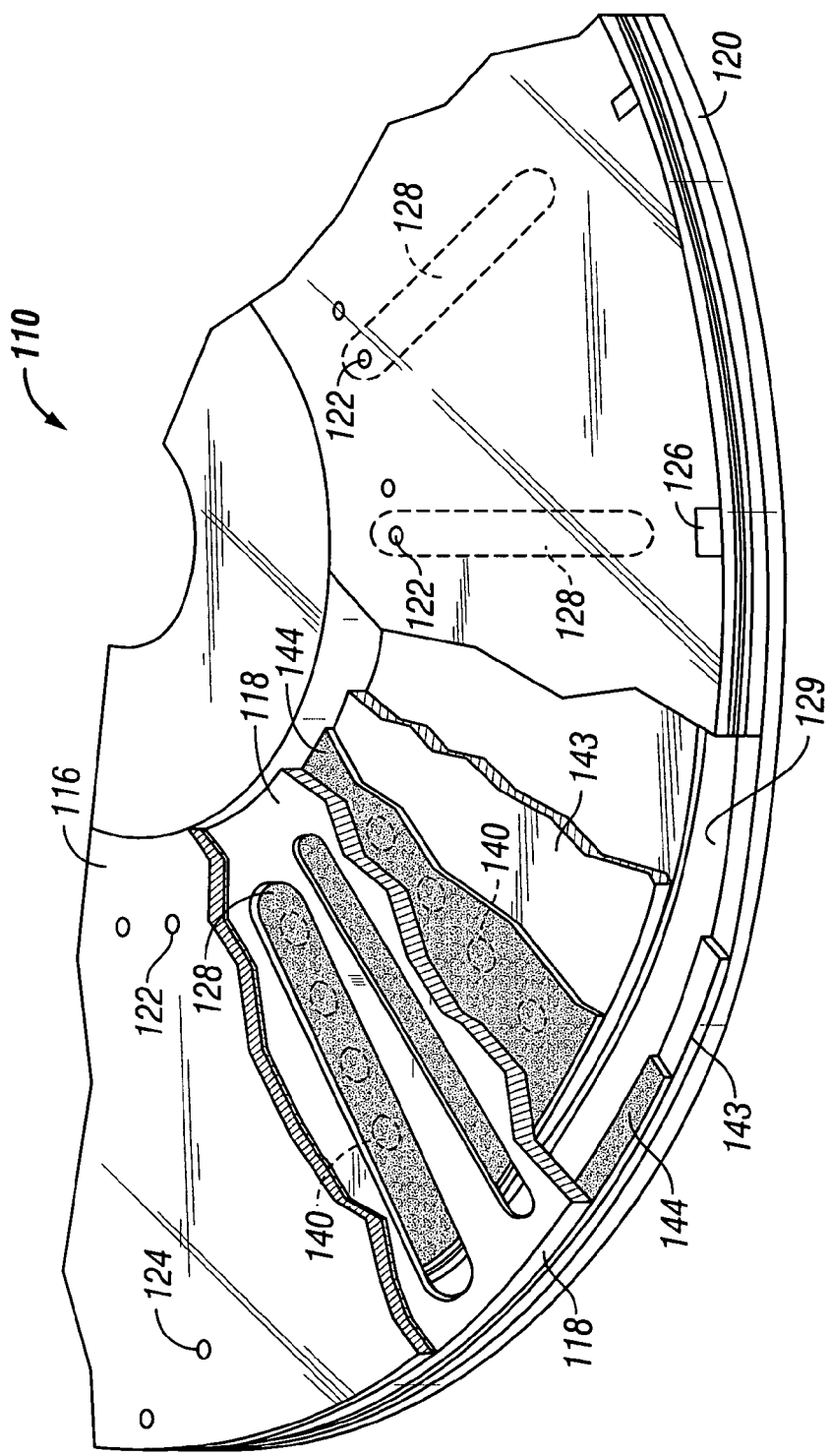
Figure 15:
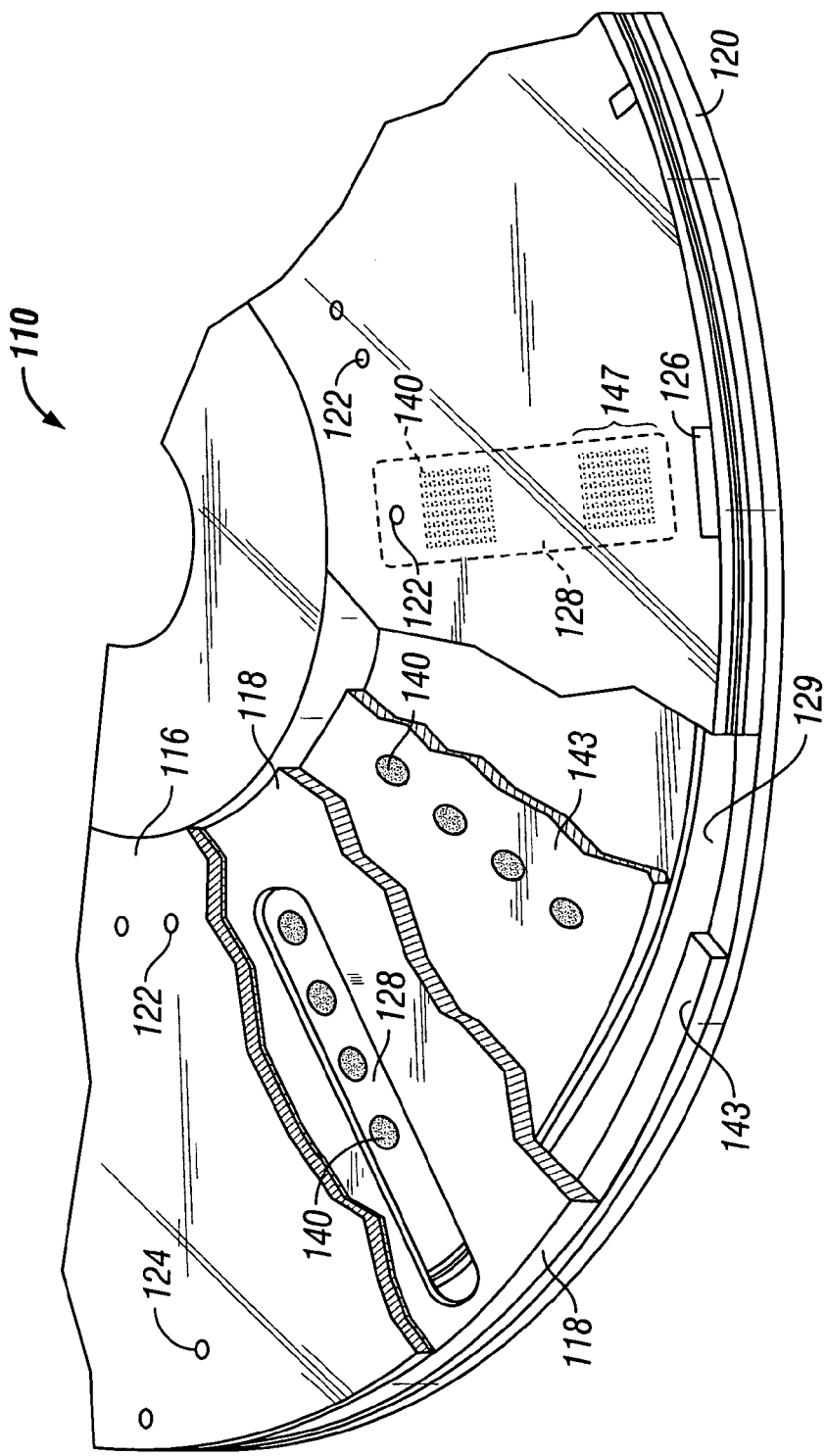
Figure 16:
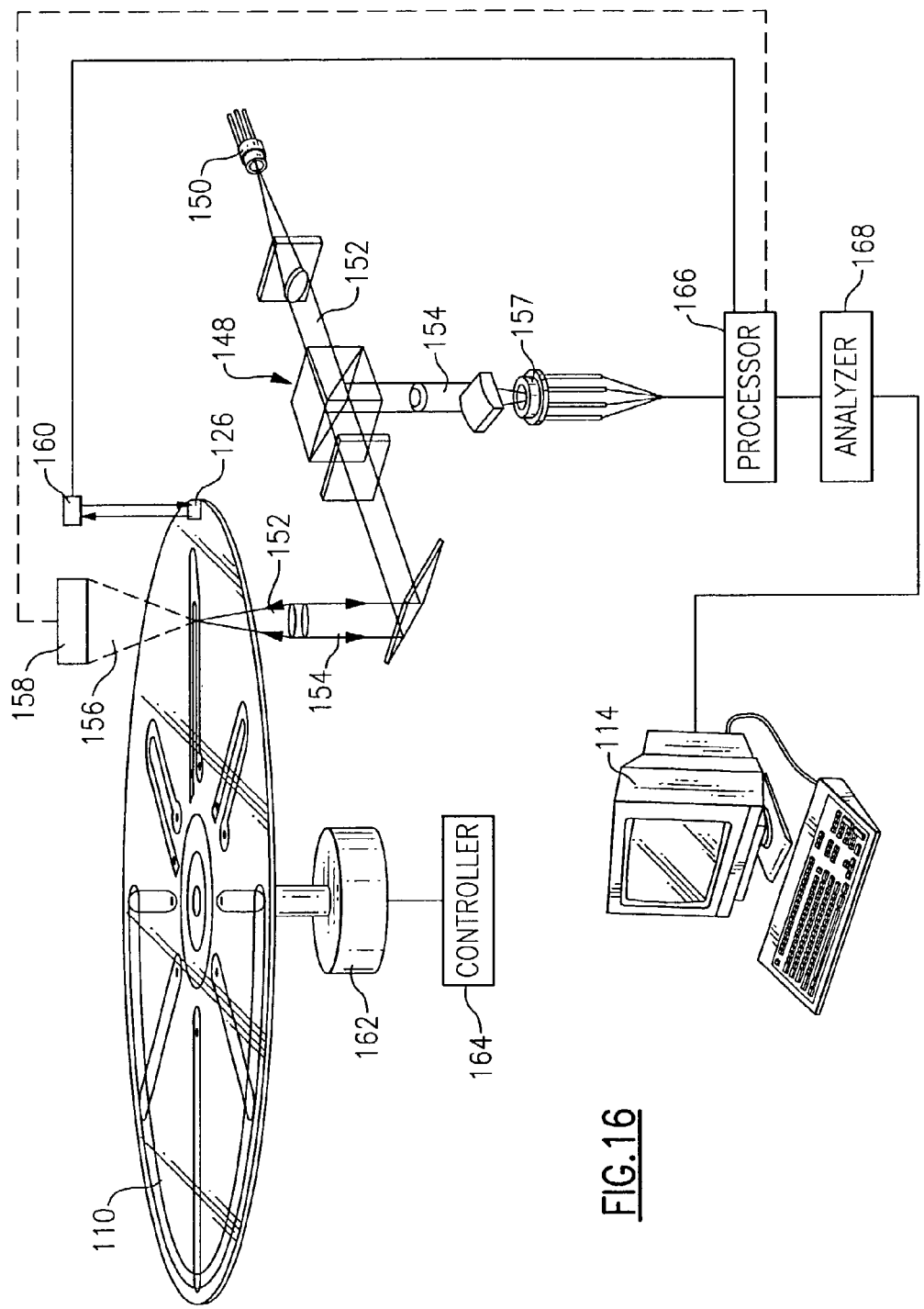
Figure 17A:
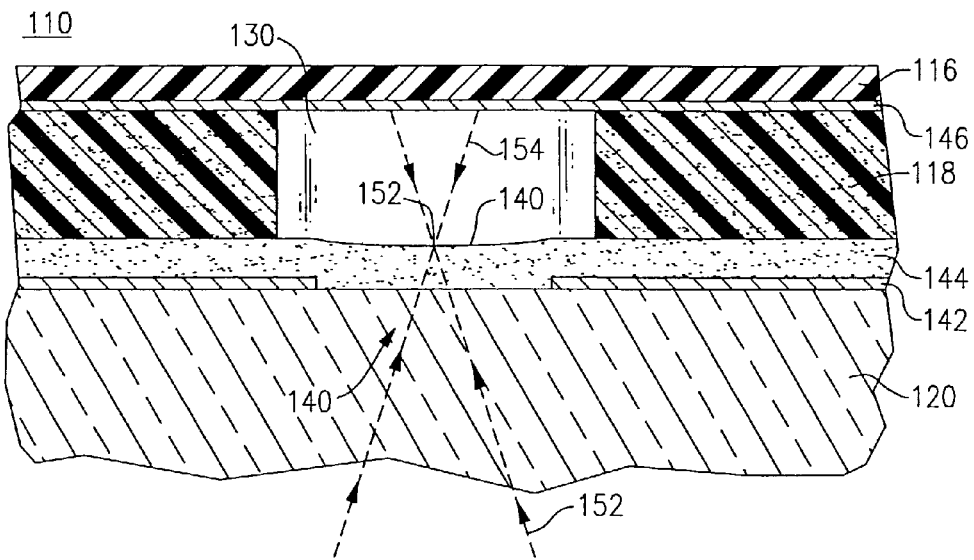
Figure 18A:
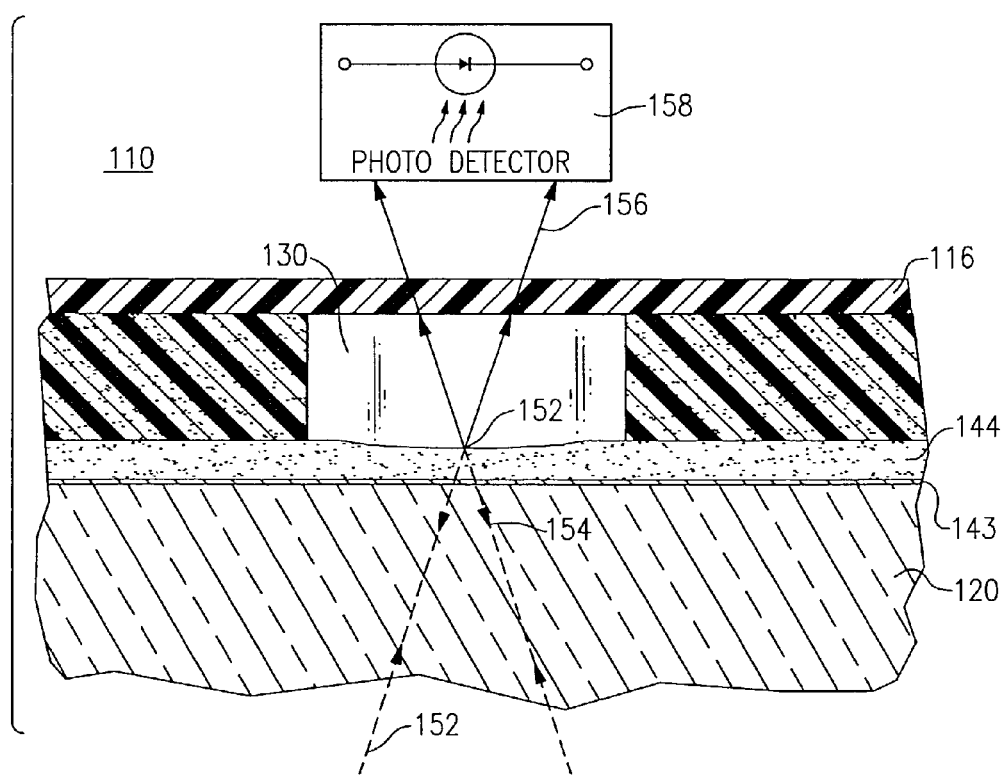
Figure 17B:
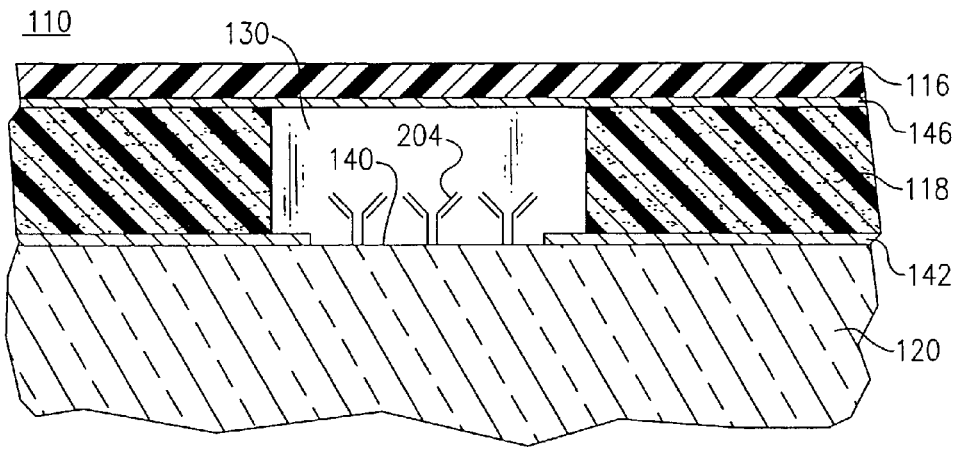
Figure 18B:
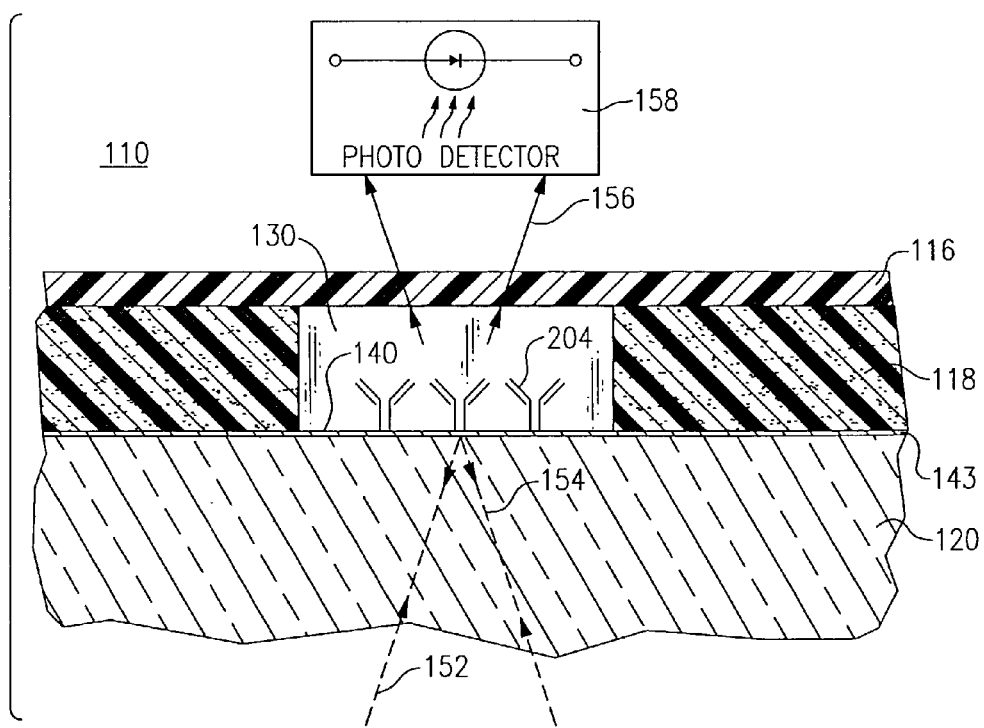
Figure 24A:
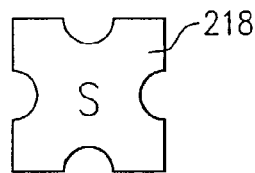
Figure 24B:
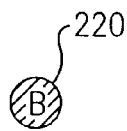
Figure 24C:
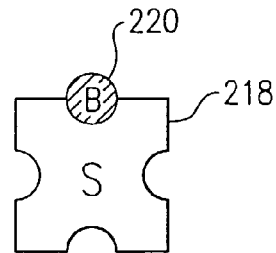
Figure 24D:
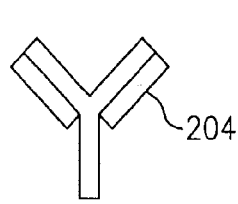
Figure 24E:
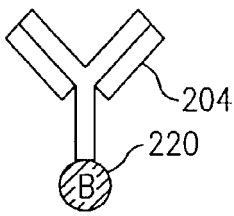
Figure 24F:
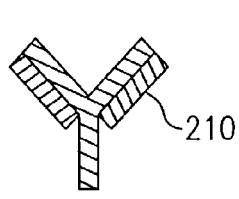
Figure 24G:
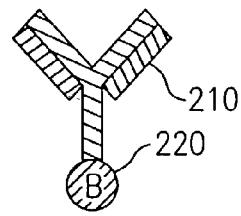
Figure 25A:
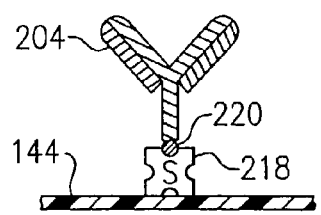
Figure 25B:
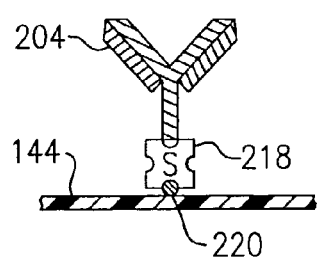
Figure 26:
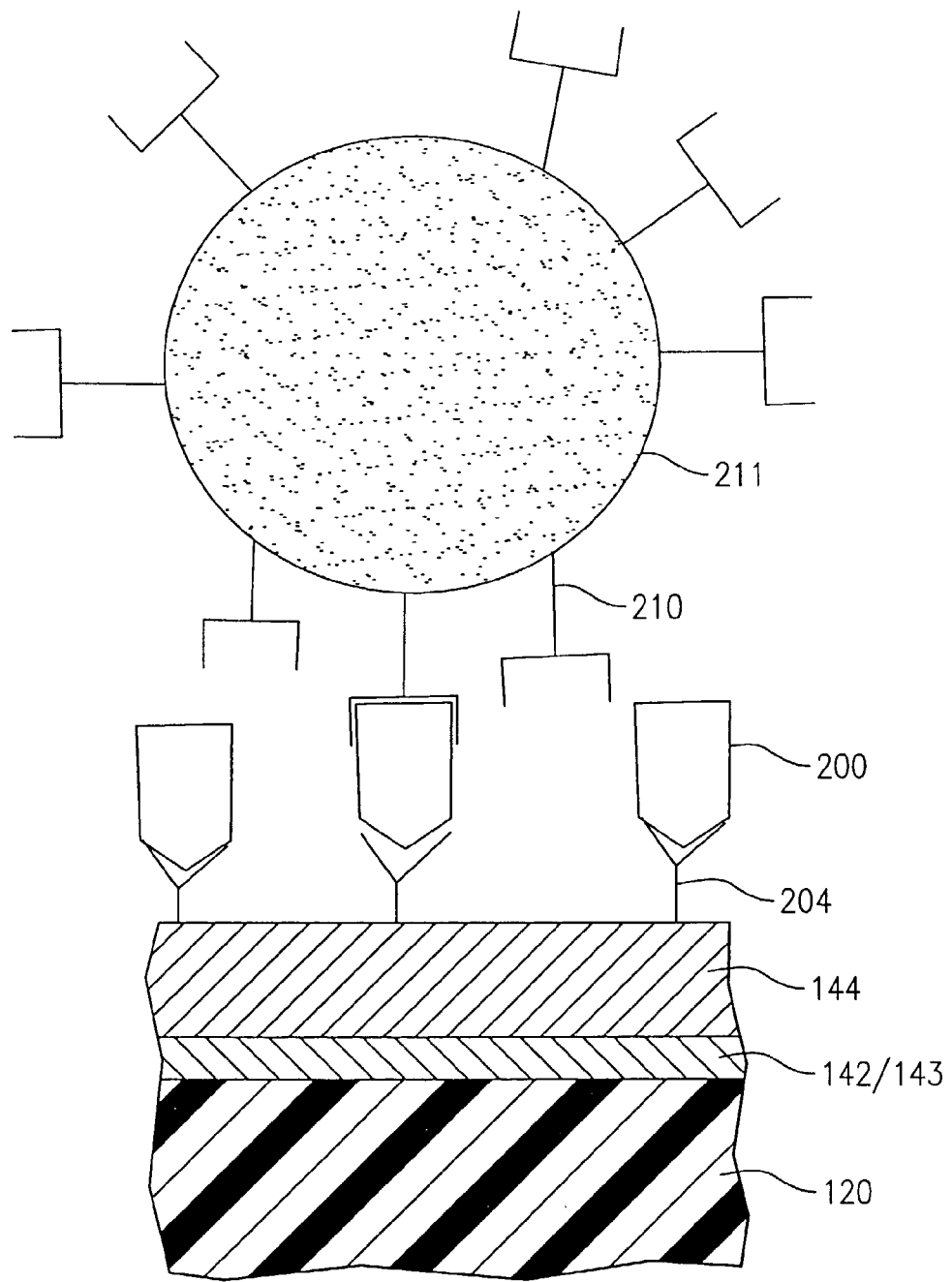

FIGS. 11A, 11B, and 11C are perspective views of three different embodiments of the substrate element of the reservoir optical bio-disc according to the present invention;

FIG. 12 is a perspective view of a pair of concentric peripheral-circumferential reservoirs as implemented in the cap member of a reservoir optical bio-disc according another aspect of the present invention;

FIG. 13 is a top plan view of a reservoir optical bio-disc assembly in the transmissive format utilizing the substrate member of FIG. 11A including absorber pads positioned within the outer reservoir;

FIG. 14 is a perspective view of the optical bio-disc illustrated in FIG. 13 with cut-away sections showing the different layers of the optical bio-disc including the type of semi-reflective layer shown in FIG. 6;

FIG. 15 is a view similar to FIG. 14 with cut-away sections showing different layers of an alternate embodiment of a reservoir optical bio-disc utilizing optical bio-discrete capture zones rather than an active layer;

FIG. 16 is a perspective and block diagram representation illustrating the system of FIG. 1 in more detail;

FIG. 17A is a partial cross sectional view taken perpendicular to a radius of the reflective optical bio-disc illustrated in FIGS. 2, 3, and 4 or the reservoir optical bio-discs in FIGS. 10–14 when implemented in a reflective format;

FIG. 17B is a partial cross sectional view taken perpendicular to a radius of an optical bio-disc in the reflective format showing capture antibodies attached within a flow channel of the optical bio-disc;

FIG. 18A is a partial cross sectional view taken perpendicular to a radius of the transmissive optical bio-disc illustrated in FIGS. 5, 8, and 9 or the reservoir optical bio-discs in FIGS. 10–14 when implemented in a transmissive format;

FIG. 18B is a partial cross sectional view taken perpendicular to a radius of an optical bio-disc in the transmissive format showing capture antibodies attached within a flow channel of the optical bio-disc;

FIG. 19 is a partial longitudinal cross sectional view representing the reflective format optical bio-discs of the present invention illustrating a wobble groove formed therein;

FIG. 20 is a partial longitudinal cross sectional view representing the transmissive format optical bio-discs of the present invention illustrating a wobble groove formed therein and a top detector;

FIG. 21 is a view similar to FIG. 17A showing the entire thickness of the reflective optical bio-disc and the initial refractive property thereof;

FIG. 22 is a view similar to FIG. 18A showing the entire thickness of the transmissive optical bio-disc and the initial refractive property thereof;

FIGS. 23A–23D are pictorial representations of various chemical elements utilized in performing immunoassays;

FIG. 24A is a pictorial representation of streptavidin;

FIG. 24B is a pictorial representation of biotin;

FIG. 24C is a pictorial representation of the cross-linking system consisting of streptavidin and biotin;

FIG. 24D is a pictorial representation of a capture antibody;

FIG. 24E is a pictorial representation of a biotinylated capture antibody;

FIG. 24F is a pictorial representation of a signal antibody;

FIG. 24G is a pictorial representation of a biotinylated signal antibody;

FIGS. 25A and 25B are pictorial representations each showing a capture antibody bound to a substrate by a cross-linking system;

FIG. 26 is an enlarged detailed partial cross sectional view illustrating the components of the optical bio-disc and related chemistries of the present invention;

FIGS. 27A–27G are cross-sectional side views of an optical bio-disc showing the steps of a method for performing an immunochemical assay according to certain aspects of the present invention; and FIGS. 28A–28D are cross-sectional side views of an optical bio-disc showing the steps of another method for performing an immunochemical assay according to other aspects of the present invention.

DETAILED DESCRIPTION OF THE INVENTION

The present invention is directed to disc drive systems, optical bio-discs, binding assays, including, for example, immunoassays, and related detection methods and software. Each of these aspects of the present invention is optical bio-discussed below in further detail.

Drive System and Related Optical Bio-discs

FIG. 1 is a perspective view of an optical bio-disc 110 according to the present invention as implemented to conduct the biological assays optical bio-disclosed herein. The present optical bio-disc 110 is shown in conjunction with an disc drive 112 and a display monitor 114.

FIG. 2 is an exploded perspective view of the principal structural elements of the optical bio-disc 110. According to one embodiment of the present invention, the optical bio-disc is a reflective zone optical bio-disc (hereinafter "reflective optical bio-disc" or "optical bio-disc in reflective format"). The principal structural elements include a cap portion 116, an adhesive member or channel layer 118, and a substrate 120. The cap portion 116 includes one or more inlet ports 122 and one or more vent ports 124. The cap portion 116 may be formed from polycarbonate and is preferably coated with a reflective surface 146 (as better illustrated in FIG. 4) on the bottom thereof as viewed from the perspective of FIG. 2. In the preferred embodiment, trigger marks or markings 126 are included on the surface of the reflective layer. Trigger markings 126 may include a clear window in all three layers of the optical bio-disc, an opaque area, or a reflective or semi-reflective area encoded with information that sends data to a processor 166, as shown in FIG. 16, that in turn interacts with the operative functions of the interrogation or incident beam 152, FIGS. 6 and 16.

The second element shown in FIG. 2 is an adhesive member 118 having fluidic circuits 128 or U-channels formed therein. The fluidic circuits 128 are formed by stamping or cutting the membrane to remove the plastic film and form the shapes as indicated. Each of the fluidic circuits 128 includes a flow channel 130 and a return channel 132. Some of the fluidic circuits 128 illustrated in FIG. 2 include a mixing chamber 134. Two different types of mixing chambers 134 are illustrated. The first is a symmetric mixing chamber 136 that is symmetrically formed relative to the flow channel 130. The second is an off-set mixing chamber 138. The off-set mixing chamber 138 is formed to one side of the flow channel 130 as indicated.

The third element illustrated in FIG. 2 is a substrate 120 including target or capture zones 140. The substrate 120 is preferably made of polycarbonate and has a reflective metal layer 142 deposited on the top thereof as also illustrated in FIG. 4. The target zones 140 are formed by removing the reflective layer 142 in the indicated shape or alternatively in any desired shape. Alternatively, the target zone 140 may be formed by a masking technique that includes masking the target zone 140 area before applying the reflective layer 142. The reflective layer 142 may be formed from a metal such as aluminum, gold, silver, nickel, and reflective metal alloys.

FIG. 3 is a top plan view of the optical bio-disc 110 illustrated in FIG. 2 with the reflective layer 142 on the cap portion 116 shown as transparent to reveal the fluidic circuits 128, the target zones 140, and trigger markings 126 situated within the optical bio-disc.

FIG. 4 is an enlarged perspective view of the reflective zone type optical bio-disc 110 according to one embodiment of the present invention. This view includes a portion of the various layers thereof, cut away to illustrate a partial sectional view of each principal layer, substrate, coating, or membrane. FIG. 4 shows the substrate 120 that is coated with the reflective layer 142. An active layer 144 may be applied over the reflective layer 142. In the preferred embodiment, the active layer 144 may be formed from polystyrene. Alternatively, polycarbonate, gold, activated glass, modified glass, or modified polystyrene, for example, polystyrene-co-maleic anhydride, may be used. The active layer 144 may also be preferably formed through derivatization of the reflective layer 142 with self assembling monolayers such as, for example, dative binding of functionally active mercapto compounds on gold and binding of functionalized silicone compounds on aluminum. In addition hydrogels can be used. Alternatively, as illustrated in this embodiment, the plastic adhesive member 118 is applied over the active layer 144. If the active layer is not present, the adhesive member 118 is applied directly to the reflective metal layer 142. The exposed section of the plastic adhesive member 118 illustrates the cut out or stamped U-shaped form that creates the fluidic circuits 128. The final principal structural layer in this reflective zone embodiment of the present optical bio-disc is the cap portion 116. The cap portion 116 includes the reflective surface 146 on the bottom thereof. The reflective surface 146 may be made from a metal such as aluminum or gold.

FIG. 5 is an exploded perspective view of the principal structural elements of an optical bio-disc 110. According to another embodiment of the present invention, the optical bio-disc is a transmissive type of optical bio-disc. The principal structural elements of the transmissive type of optical bio-disc 110 similarly include the cap portion 116, the adhesive member 118, and the substrate 120 layer. The cap portion 116 includes one or more inlet ports 122 and one or more vent ports 124. The cap portion 116 may be formed from a polycarbonate layer. Optional trigger markings 126 may be included on the surface of a thin semi-reflective metal layer 143, as best illustrated in FIGS. 6 and 9. Trigger markings 126 may include a clear window in all three layers of the optical bio-disc, an opaque area, or a reflective or semi-reflective area encoded with information that sends data to the processor 166, FIG. 16, which in turn interacts with the operative functions of the interrogation beam 152, FIGS. 6 and 16.

The second element shown in FIG. 5 is the adhesive member or channel layer 118 having fluidic circuits 128 or U-channels formed therein. The fluidic circuits 128 are formed by stamping or cutting the membrane to remove plastic film and form the shapes as indicated. Each of the fluidic circuits 128 includes the flow channel 130 and the return channel 132. Some of the fluidic circuits 128 illustrated in FIG. 5 include the mixing chamber 134. Two different types of mixing chambers 134 are illustrated. The first is the symmetric mixing chamber 136 that is symmetrically formed relative to the flow channel 130. The second is the off-set mixing chamber 138. The off-set mixing chamber 138 is formed to one side of the flow channel 130 as indicated.

The third element illustrated in FIG. 5 is the substrate 120 which may include the target or capture zones 140. The substrate 120 is preferably made of polycarbonate and has the thin semi-reflective metal layer 143 deposited on the top thereof in FIG. 6. The semi-reflective layer 143 associated with the substrate 120 of the optical bio-disc 110 illustrated in FIGS. 5 and 6 is significantly thinner than the reflective layer 142 on the substrate 120 of the reflective optical bio-disc 110 illustrated in FIGS. 2, 3 and 4. The thinner semi-reflective layer 143 allows for some transmission of the interrogation beam 152 through the structural layers of the transmissive optical bio-disc as shown in FIG. 11. The thin semi-reflective layer 143 may be formed from a metal such as aluminum or gold.

FIG. 6. is an enlarged perspective view of the substrate 120 and semi-reflective layer 143 of the transmissive embodiment of the optical bio-disc 110 illustrated in FIG. 5. The thin semi-reflective layer 143 may be made from a metal such as aluminum or gold. In the preferred embodiment, the thin semi-reflective layer 143 of the transmissive optical bio-disc illustrated in FIGS. 5 and 6 is approximately 100–300 Å thick and does not exceed 400 Å. This thinner semi-reflective layer 143 allows a portion of the incident or interrogation beam 152 to penetrate and pass through the semi-reflective layer 143 to be detected by a top detector 158, FIG. 16, while some of the light is reflected or returned back along the incident path. As indicated below, Table 1 presents the reflective and transmissive characteristics of a gold film relative to the thickness of the film. The gold film layer is fully reflective at a thickness greater than 800 Å. While the threshold density for transmission of light through the gold film is approximately 400 Å.

TABLE 1

Au film Reflection and Transmission (Absolute Values)

| Thickness (Angstroms) | Thickness (nm) | Reflectance | Transmittance |
| --- | --- | --- | --- |
| 0 | 0 | 0.0505 | 0.9495 |
| 50 | 5 | 0.1683 | 0.7709 |
| 100 | 10 | 0.3981 | 0.5169 |
| 150 | 15 | 0.5873 | 0.3264 |
| 200 | 20 | 0.7142 | 0.2057 |
| 250 | 25 | 0.7959 | 0.1314 |
| 300 | 30 | 0.8488 | 0.0851 |
| 350 | 35 | 0.8836 | 0.0557 |
| 400 | 40 | 0.9067 | 0.0368 |
| 450 | 45 | 0.9222 | 0.0244 |
| 500 | 50 | 0.9328 | 0.0163 |
| 550 | 55 | 0.9399 | 0.0109 |
| 600 | 60 | 0.9448 | 0.0073 |
| 650 | 65 | 0.9482 | 0.0049 |
| 700 | 70 | 0.9505 | 0.0033 |
| 750 | 75 | 0.9520 | 0.0022 |
| 800 | 80 | 0.9531 | 0.0015 |

Figure 7:
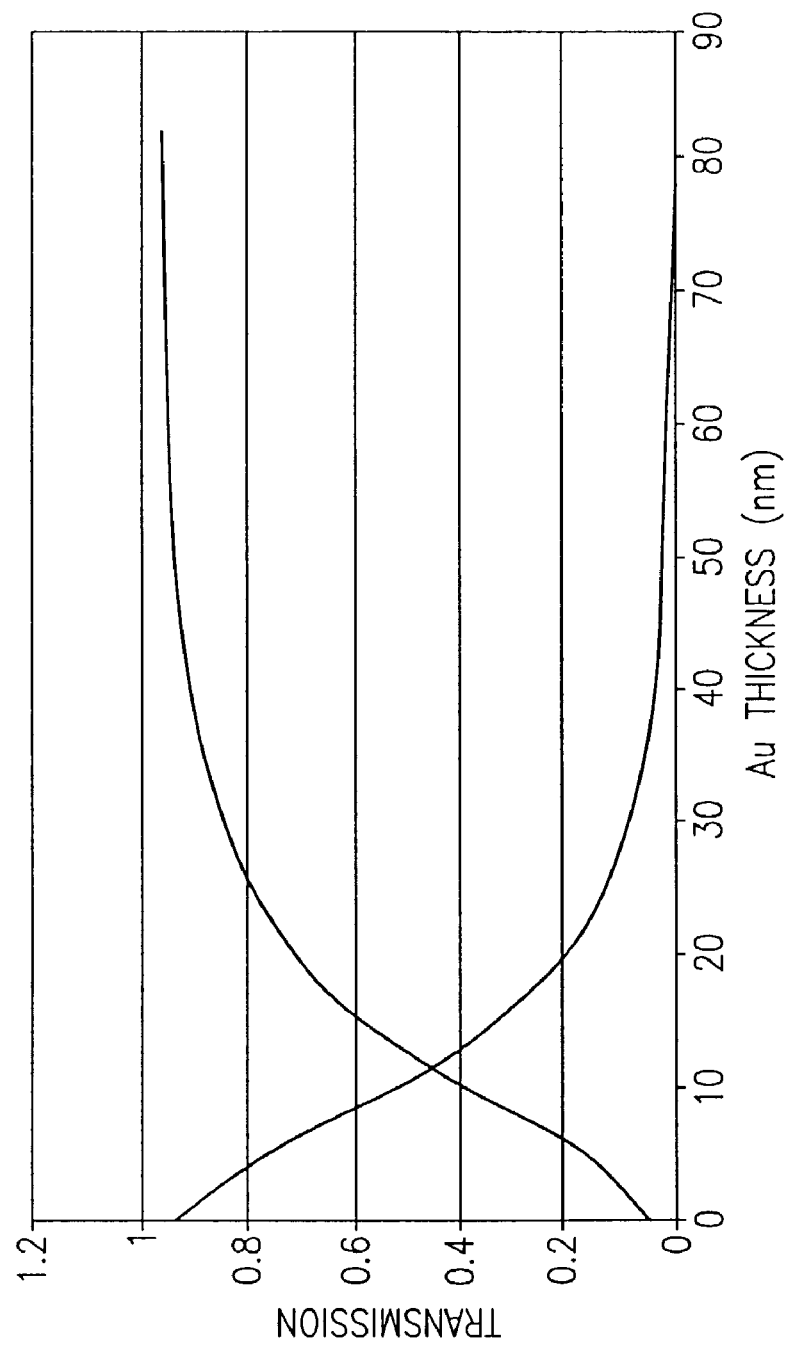
FIG. 7 is a graphical representation showing the relationship between thickness and transmission of a thin gold film.

In addition to Table 1, FIG. 7 provides a graphical representation of the inverse proportion of the reflective and transmissive nature of the thin semi-reflective layer 143 based upon the thickness of the gold. Reflective and transmissive values used in the graph illustrated in FIG. 7 are absolute values.

FIG. 8 is a top plan view of the transmissive type optical bio-disc 110 illustrated in FIGS. 5 and 6 with the transparent cap portion 116 revealing the fluidic channels, the trigger markings 126, and the target zones 140 as situated within the optical bio-disc.

FIG. 9 is an enlarged perspective view of the optical bio-disc 110 according to the transmissive optical bio-disc embodiment of the present invention. The optical bio-disc 110 is illustrated with a portion of the various layers thereof cut away to illustrate a partial sectional view of each principal layer, substrate, coating, or membrane. FIG. 9 illustrates a transmissive optical bio-disc format with the clear cap portion 116, the thin semi-reflective layer 143 on the substrate 120, and trigger markings 126. Trigger markings 126 include opaque material placed on the top portion of the cap. Alternatively the trigger marking 126 may be formed by clear, non-reflective windows etched on the thin reflective layer 143 of the optical bio-disc, or any mark that absorbs or does not reflect the signal coming from the trigger detector 160 in FIG. 16.

FIG. 9 also shows, the target zones 140 formed by marking the designated area in the indicated shape or alternatively in any desired shape. Markings to indicate target zone 140 may be made on the thin semi-reflective layer 143 on the substrate 120 or on the bottom portion of the substrate 120 (under the optical bio-disc). Alternatively, the target zones 140 may be formed by a masking technique that includes masking the entire thin semi-reflective layer 143 except the target zones 140. In this embodiment, target zones 140 may be created by silk screening ink onto the thin semi-reflective layer 143. An active layer 144 may be applied over the thin semi-reflective layer 143. In the preferred embodiment, the active layer 144 is a 40 to 200 µm thick layer of 2% polystyrene. Alternatively, polycarbonate, gold, activated glass, modified glass, or modified polystyrene, for example, polystyrene-co-maleic anhydride, may be used. The active layer 144 may also be preferably formed through derivatization of the reflective layer 143 with self assembling monolayers such as, for example, dative binding of functionally active mercapto compounds on gold and binding of functionalized silicone compounds on aluminum. In addition hydrogels can be used. As illustrated in this embodiment, the plastic adhesive member 118 is applied over the active layer 144. If the active layer 144 is not present, the adhesive member 118 is directly applied over the semi-reflective metal layer 143. The exposed section of the plastic adhesive member 118 illustrates the cut out or stamped U-shaped form that creates the fluidic circuits 128. The final principal structural layer in this transmissive embodiment of the present optical bio-disc 110 is the clear, non-reflective cap portion 116 that includes inlet ports 122 and vent ports 124.

Figure 10:
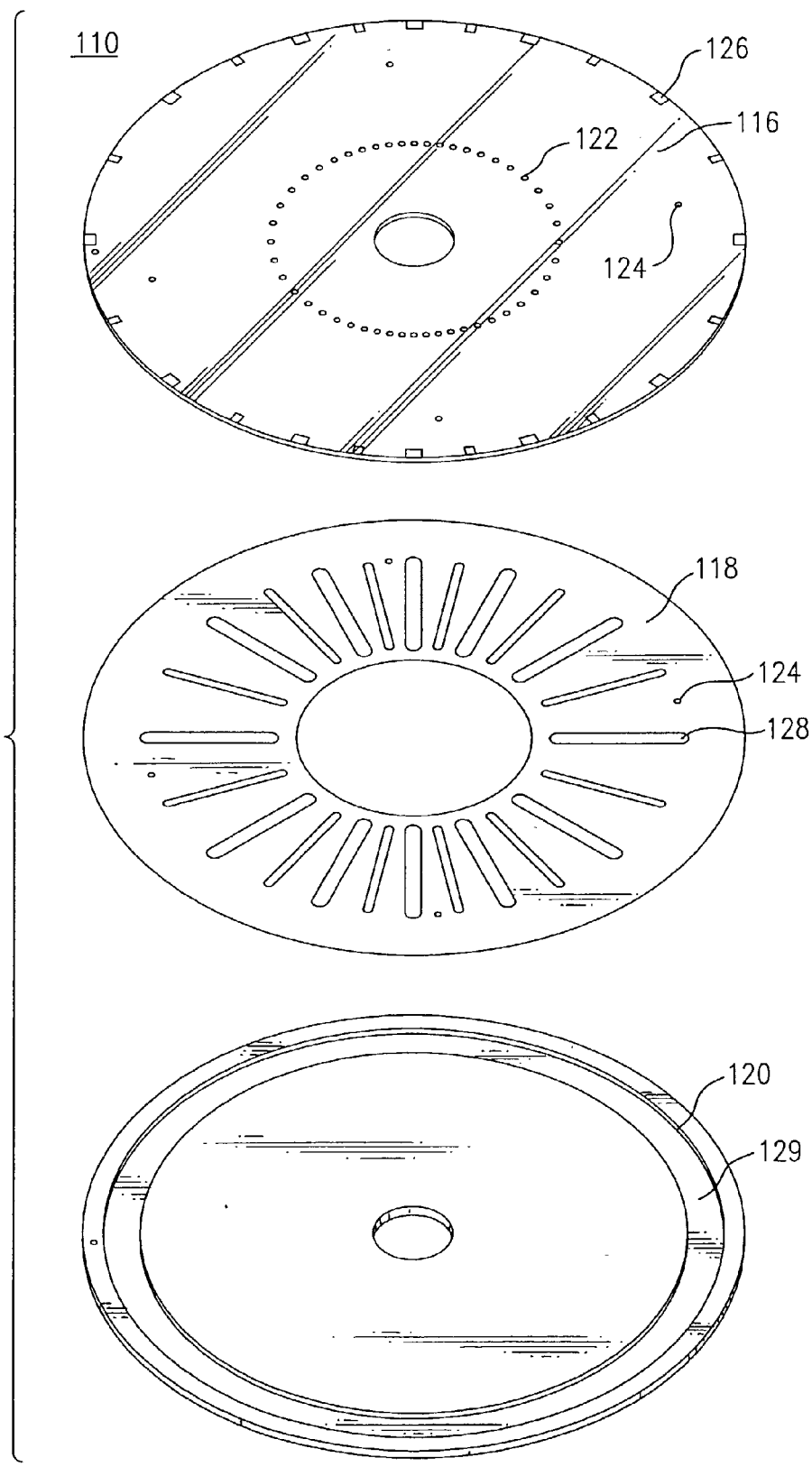
FIG. 10 is an exploded perspective view of a peripheral-circumferential reservoir optical bio-disc (hereinafter "reservoir optical bio-disc") as employed in conjunction with the present invention.

FIG. 10 is an exploded perspective view of the principal structural elements of yet another embodiment of the optical bio-disc 110 of the present invention. This embodiment is generally referred to herein as a "reservoir optical bio-disc". This embodiment may be implemented in either the reflective or transmissive formats optical bio-discussed above. In the alternative, the optical bio-disc according to the invention may be implement as a hybrid optical bio-disc that has both transmissive and reflective formats and further any desired combination of fluidic channels and circumferencial reservoirs.

The principal structural elements of this reservoir embodiment similarly include a cap portion 116, an adhesive member or channel layer 118, and a substrate 120. The cap portion 116 includes one or more inlet ports 122 and one or more vent ports 124. The vent ports 124 allows venting of air in the fluidic channels or fluidic circuits of the optical bio-disc thereby preventing air blocks within the fluidic circuits when the optical bio-disc is in use. The cap portion 116 is preferably formed from polycarbonate and may be either left clear or coated with a reflective surface 146 when implemented in the reflective format as in FIG. 4. In the preferred embodiment reflective reservoir optical bio-disc, trigger markings 126 are included on the surface of the reflective layer 142. Trigger markings 126 may include a clear window in all three layers of the optical bio-disc, an opaque area, or a reflective or semi-reflective area encoded with information that sends data to a processor 166, as shown in FIG. 16, that in turn interacts with the operative functions of the interrogation or incident beam 152, FIGS. 6 and 16. According to one aspect of the present invention, trigger markings 126 are as wide as the respective fluidic circuits 128.

The second element shown in FIG. 10 is the adhesive member or channel layer 118 having fluidic circuits or straight channels 128 formed therein. According to one embodiment of the present invention, these fluidic circuits 128 are directed along the radii of the optical bio-disc as illustrated. The fluidic circuits 128 are formed by stamping or cutting the membrane to remove the plastic film and form the shapes as indicated.

The third element illustrated in FIG. 10 is the substrate 120. The substrate 120 is preferably made of polycarbonate and has either the reflective metal layer 142 or the thin semi-reflective metal layer 143 deposited on the top thereof depending on whether the reflective or transmissive format is desired. As indicated above, layers 142 or 143 may be formed from a metal such as aluminum, gold, silver, nickel, and reflective metal alloys. The substrate 120 is provided with a reservoir 129 along the outer edge that is preferably implemented as the peripheral-circumferential reservoir 129 as illustrated.

FIGS. 11A, 11B, and 11C are different embodiments of substrate 120 including a variety of different implementations of the reservoir aspect of the present invention. More specifically, FIG. 11A shows the substrate 120 including two concentric reservoirs separated by raised portions or land segments 135. As illustrated, this embodiment includes an inner reservoir 131 and an outer reservoir 133. These raised portions or land segments 135 are arcuate in shape as shown and are arranged to form openings or passthrough ports 137 at preferably regular intervals to thereby place the inner reservoir 131 and an outer reservoir 133 in fluid commination with each other.

With reference now to FIG. 11B, there is shown another embodiment of substrate 120 including segmented or divided circumferential reservoirs 139. Each of these independent arcuate shaped reservoirs 139 are fluidly isolated or separated from one another by elevated portions of the substrate 120 as shown. FIG. 11B shows 4 independent arcuate shaped reservoirs 139 for illustrative purposes. As one skilled in the art will appreciate, however, any desired number reservoirs and configurations may be implemented.

Referring next to FIG. 11C, there is shown a modified embodiment of substrate 120 of FIG. 11A. In this embodiment, substrate 120 has one or more mixing wells 141. The mixing wells 141 may be circular or radially directed as illustrated.

FIG. 12 illustrates an alternate embodiment of cap portion 116. In this embodiment, the reservoir system illustrated in FIG. 11A is formed in the cap 116 as illustrated rather than in the substrate 120. As would be readily apparent to one of skill in the art given the present optical bio-disclosure, the reservoir systems illustrated in FIGS. 11B and 11C could similarly be formed in the cap 116.

FIG. 13 is a top plan view of a reservoir optical bio-disc embodiment of the optical bio-disc 110 including the peripheral reservoir system shown in FIGS. 11A and 12 as implemented in the transmissive format. In the top plan in FIG. 13, the cap portion 116 is shown as being transparent to show channels 128 and other structures. As illustrated, the three principal structural elements are assembled wherein the cap portion 116 is the top layer, adhesive portion 118 is the middle layer, and substrate 120 is the bottom layer. According to one or more modified embodiments of the optical bio-disc assembly shown in FIG. 13, the reservoir system may be of the type shown in any one of FIGS. 11A, 11B, and 11C as formed in either the cap 116 or substrate 120.

As shown generally in FIGS. 13, 14, and 15, the fluidic channel 128 is placed in fluid communication with the reservoir 129 or 131. In this manner, fluid deposited in the inlet port 122 is directed through the channel 128 and then into the reservoir 129 or 131 during processing of the assay in the disc drive. In the embodiment shown in FIG. 13, waste fluid is further directed to the outer reservoir 133 by way of pass through ports 137 and then optionally into absorber pads 145. Absorber pads 145 may be optionally filled with drying agents or desiccants to keep all reagents deposited in the optical bio-disc 110 free of moisture to preserve functional activity of the reagents and increase the shelf life of the optical bio-disc 110.

In accordance with a more particular embodiment of the present invention, the reservoir may include one or more absorber pads 145 as illustrated in FIG. 13. The absorber pads may be preferably formed form a material such as cellulose glass fiber, or any other type of suitable absorbing material. The pads 145 are preferably evenly distributed around the reservoir to thereby promote and maintain balance of the optical bio-disc while in use during rotation in the drive Moving on now specifically to FIG. 14, there is presented an enlarged perspective view of the optical bio-disc 110 according to the reservoir optical bio-disc embodiment of the present invention. The optical bio-disc 110 is illustrated with a portion of the various layers thereof cut away to illustrate a partial sectional view of each principal layer, substrate, coating, or membrane. FIG. 14 illustrates a reservoir optical bio-disc in the transmissive format with the clear cap portion 116, the thin semi-reflective layer 143 on the substrate 120, and trigger markings 126. Trigger markings 126 include opaque material placed on the top portion of the cap. Alternatively the trigger marking 126 may be formed by clear, non-reflective windows etched on the thin reflective layer 143 of the optical bio-disc, or any mark that absorbs or does not reflect the signal coming from the trigger detector 160 in FIG. 16.

FIG. 14 also shows an active layer 144 that may be applied over the thin semi-reflective layer 143. In the preferred embodiment, the active layer 144 is a 40 to 200 µm thick layer of 2% polystyrene. Alternatively, polycarbonate, gold, activated glass, modified glass, or modified polystyrene, for example, polystyrene-co-maleic anhydride, may be used. The active layer 144 may also be preferably formed through derivatization of the reflective layer 142 with self assembling monolayers such as, for example, dative binding of functionally active mercapto compounds on gold and binding of functionalized silicone compounds on aluminum. In addition hydrogels can also be used. As illustrated in this embodiment, the plastic adhesive member 118 is applied over the active layer 144. If the active layer 144 is not present, the adhesive member 118 is directly applied over the semi-reflective metal layer 143 as shown in FIG. 15 which is optical bio-discussed in further detail below. The exposed section of the plastic adhesive member 118 illustrates the cut out or stamped straight shaped form that creates the fluidic circuits 128. The exposed section of the substrate 120 illustrates the peripheral circumferential reservoir 129. The final principal structural layer in this embodiment of the present optical bio-disc 110 is the clear, non-reflective cap portion 116 that includes inlet ports 122 and vent ports 124. As would be readily apparent to one of skill in the art given the present optical bio-disclosure, the various embodiments of the substrate 120, illustrated in FIGS. 11A, 11B, and 11C could be used as the substrate of the optical bio-disc illustrated in FIG. 14.

FIG. 15 is a view similar to FIG. 14 showing an alternate embodiment of the transmissive reservoir optical bio-disc using optical bio-discrete capture zones 140 rather than an active layer 144. The optical bio-discrete capture zones 140 may be positioned at any pre-determined locations on the metal layer 143 and distributed in the fluidic circuit 128 as illustrated. FIG. 15 further shows, a wide-format straight channel 128 having several optical bio-discrete capture zones 140 arranged in a micro-array format 147. According to an embodiment of the present invention, the fluidic circuit 128 of FIG. 15 is wide enough to accommodate multiple sets of a micro arrays 147 from a minimum size of 2×2 capture zones to in excess of 1,000×1,000 capture zones. As would also be readily apparent to one of skill in the art given the present optical bio-disclosure, the various embodiments of the substrate 120, illustrated in FIGS. 11A, 11B, and 11C could also be used as the substrate of the optical bio-disc illustrated in FIG. 15.

FIG. 16 is a representation in perspective and block diagram illustrating optical components 148, a light source 150 that produces the incident or interrogation beam 152, a return beam 154, and a transmitted beam 156. In the case of the reflective optical bio-disc illustrated in FIG. 4, the return beam 154 is reflected from the reflective surface 146 of the cap portion 116 of the optical bio-disc 110. In this reflective embodiment of the present optical bio-disc 110, the return beam 154 is detected and analyzed for the presence of signal agents by a bottom detector 157. In the transmissive optical bio-disc format, on the other hand, the transmitted beam 156 is detected, by a top detector 158, and is also analyzed for the presence of signal agents. In the transmissive embodiment, a photo detector may be used as a top detector 158.

FIG. 16 also shows a hardware trigger mechanism that includes the trigger markings 126 on the optical bio-disc and a trigger detector 160. The hardware triggering mechanism is used in both reflective optical bio-discs (FIG. 4) and transmissive optical bio-discs (FIGS. 9, 14, and 15). The triggering mechanism allows the processor 166 to collect data only when the interrogation beam 152 is on a respective target zone 140. Furthermore, in the transmissive optical bio-disc system, a software trigger may also be used. The software trigger uses the bottom detector to signal the processor 166 to collect data as soon as the interrogation beam 152 hits the edge of a respective target zone 140. FIG. 16 also illustrates a drive motor 162 and a controller 164 for controlling the rotation of the optical bio-disc 110. FIG. 16 further shows the processor 166 and analyzer 168 implemented in the alternative for processing the return beam 154 and transmitted beam 156 associated the transmissive optical bio-disc.

FIG. 17A is a partial cross sectional view of the reflective optical bio-disc embodiment of the optical bio-disc 110 according to the present invention. FIG. 17A illustrates the substrate 120 and the reflective layer 142. As indicated above, the reflective layer 142 may be made from a material such as aluminum, gold or other suitable reflective material. In this embodiment, the top surface of the substrate 120 is smooth. FIG. 17A also shows the active layer 144 applied over the reflective layer 142. As shown in FIG. 17A, the target zone 140 is formed by removing an area or portion of the reflective layer 142 at a desired location or, alternatively, by masking the desired area prior to applying the reflective layer 142. As further illustrated in FIG. 17A, the plastic adhesive member 118 is applied over the active layer 144. FIG. 17A also shows the cap portion 116 and the reflective surface 146 associated therewith. Thus when the cap portion 116 is applied to the plastic adhesive member 118 including the desired cutout shapes, flow channel 130 is thereby formed. As indicated by the arrowheads shown in FIG. 17A, the path of the incident beam 152 is initially directed toward the substrate 120 from below the optical bio-disc 110. The incident beam then focuses at a point proximate the reflective layer 142. Since this focusing takes place in the target zone 140 where a portion of the reflective layer 142 is absent, the incident continues along a path through the active layer 144 and into the flow channel 130. The incident beam 152 then continues upwardly traversing through the flow channel to eventually fall incident onto the reflective surface 146. At this point, the incident beam 152 is returned or reflected back along the incident path and thereby forms the return beam 154.

FIG. 17B is a view similar to FIG. 17A showing all the components of the reflective optical bio-disc described in FIG. 17A. FIG. 17B further shows capture antibodies 204 attached to the substrate 120 within the capture zone 140.

FIG. 18A is a partial cross sectional view of the transmissive embodiment of the optical bio-disc 110 according to the present invention. FIG. 18A illustrates a transmissive optical bio-disc format with the clear cap portion 116 and the thin semi-reflective layer 143 on the substrate 120. FIG. 18A also shows the active layer 144 applied over the thin semi-reflective layer 143. In the preferred embodiment, the transmissive optical bio-disc has the thin semi-reflective layer 143 made from a metal such as aluminum or gold approximately 100–300 Angstroms thick and does not exceed 400 Angstroms. This thin semi-reflective layer 143 allows a portion of the incident or interrogation beam 152, from the light source 150 in FIG. 16, to penetrate and pass upwardly through the optical bio-disc to be detected by a top detector 158, while some of the light is reflected back along the same path as the incident beam but in the opposite direction. In this arrangement, the return or reflected beam 154 is reflected from the semi-reflective layer 143. Thus in this manner, the return beam 154 does not enter into the flow channel 130. The reflected light or return beam 154 may be used for tracking the incident beam 152 on pre-recorded information tracks formed in or on the semi-reflective layer 143 as described in more detail in conjunction with FIGS. 19 and 20.

In the optical bio-disc embodiment illustrated in FIG. 18A, a defined target zone 140 may or may not be present. Target zone 140 may be created by direct markings made on the thin semi-reflective layer 143 on the substrate 120. These marking may be done using silk screening or any equivalent method. In the alternative embodiment where no physical indicia are employed to define a target zone, the flow channel 130 in effect is utilized as a confined target area in which inspection of an investigational feature is conducted.

FIG. 18B is a view similar to FIG. 18A showing all the components of the reflective optical bio-disc described in FIG. 18A. FIG. 18B further shows capture antibodies 204 attached to the substrate 120 within the capture zone 140.

FIG. 19 is a cross sectional view taken across the tracks of the reflective optical bio-disc embodiment of the optical bio-disc 110 according to the present invention. This view is taken longitudinally along a radius and flow channel of the optical bio-disc. FIG. 19 includes the substrate 120 and the reflective layer 142. In this embodiment, the substrate 120 includes a series of grooves 170. The grooves 170 are in the form of a spiral extending from near the center of the optical bio-disc toward the outer edge. The grooves 170 are implemented so that the interrogation beam 152 may track along the spiral grooves 170 on the optical bio-disc. This type of groove 170 is known as a "wobble groove". A bottom portion having undulating or wavy sidewalls forms the groove 170, while a raised or elevated portion separates adjacent grooves 170 in the spiral. The reflective layer 142 applied over the grooves 170 in this embodiment is, as illustrated, conformal in nature. FIG. 19 also shows the active layer 144 applied over the reflective layer 142. As shown in FIG. 19, the target zone 140 is formed by removing an area or portion of the reflective layer 142 at a desired location or, alternatively, by masking the desired area prior to applying the reflective layer 142. As further illustrated in FIG. 19, the plastic adhesive member 118 is applied over the active layer 144. FIG. 19 also shows the cap portion 116 and the reflective surface 146 associated therewith. Thus, when the cap portion 116 is applied to the plastic adhesive member 118 including the desired cutout shapes, the flow channel 130 is thereby formed.

FIG. 20 is a cross sectional view taken across the tracks of the transmissive optical bio-disc embodiment of the optical bio-disc 110 according to the present invention, as described in FIG. 18A. This view is taken longitudinally along a radius and flow channel of the optical bio-disc. FIG. 20 illustrates the substrate 120 and the thin semi-reflective layer 143. This thin semi-reflective layer 143 allows the incident or interrogation beam 152, from the light source 150, to penetrate and pass through the optical bio-disc to be detected by the top detector 158, while some of the light is reflected back in the form of the return beam 154. The thickness of the thin semi-reflective layer 143 is determined by the minimum amount of reflected light required by the optical bio-disc reader to maintain its tracking ability. The substrate 120 in this embodiment, like that optical bio-discussed in FIG. 19, includes the series of grooves 170. The grooves 170 in this embodiment are also preferably in the form of a spiral extending from near the center of the optical bio-disc toward the outer edge. The grooves 170 are implemented so that the interrogation beam 152 may track along the spiral. FIG. 20 also shows the active layer 144 applied over the thin semi-reflective layer 143. As further illustrated in FIG. 20, the plastic adhesive member 118 is applied over the active layer 144. FIG. 20 also shows the cap portion 116 without a reflective surface 146. Thus, when the cap is applied to the plastic adhesive member 118 including the desired cutout shapes, the flow channel 130 is thereby formed and a part of the incident beam 152 is allowed to pass therethrough substantially unreflected.

FIG. 21 is a view similar to FIG. 17A showing the entire thickness of the reflective optical bio-disc and the initial refractive property thereof. FIG. 22 is a view similar to FIG. 18A showing the entire thickness of the transmissive optical bio-disc and the initial refractive property thereof. Grooves 170 are not seen in FIGS. 21 and 22 since the sections are cut along the grooves 170. FIGS. 21 and 22 show the presence of the narrow flow channel 130 that are situated perpendicular to the grooves 170 in these embodiments.

FIGS. 19, 20, 21, and 22 show the entire thickness of the respective reflective and transmissive optical bio-discs. In these Figs., the incident beam 152 is illustrated initially interacting with the substrate 120 which has refractive properties that change the path of the incident beam as illustrated to provide focusing of the beam 152 on the reflective layer 142 or the thin semi-reflective layer 143.

Binding Assays on the Optical Bio-disc

There are three classes of binding assays. These include binding protein capture assays, analyte capture assays, and sandwich type assays. The latter assay type can have a binding protein-analyte-binding protein or analyte-binding protein-analyte format.

A specific implementation of a binding assay is an immunoassay. In such an immunoassay, the binding protein may be represented by a capture antibody or a capture antigen and the analyte may be an antigen/hapten or a target antibody, respectively. The product of the reaction is an antigen-antibody immune complex.

All of the following will concentrate on the immunoassay implementation of binding assays but will in most cases apply also to the broader definition of binding assays. More detailed information on immunoassays can be found in "Radioimmunoassay Methods", K. E. Kirkham and W. M. Hunter (Eds.), Churchill Livingston Edinburgh and London (1973). Both, a target antigen and a target antibody can be quantified by an immunoassay designed in analogy to one of the four formats as described below in conjunction with FIGS. 23A–23D.

Referring to FIG. 23A, there is illustrated an antibody capture assay utilizing an analyte (antigen) 200 attached to a solid support 206. A labeled or unlabelled signal antibody 202 is allowed to bind to the immobilized analyte 200. FIGS. 23A and 23C shows the labeled form of the signal antibody 202 having label 208 attached thereto.

Referring next to FIG. 23B, there is shown a pictorial representation of an antigen capture assay. In this embodiment of the present invention, antibody 202 is immobilized to a solid support 206 and labeled or unlabelled signal antigen 214 is allowed to bind to the antibody 202 on the solid phase 206. FIGS. 23B and 23D shows the labeled form of the antigen 214 having label 208 attached thereto.

Any unbound antibody or antigen in the antibody or antigen capture assays of FIGS. 23A and 23B, respectively, are removed by washing. The bound antibody or analyte is quantified directly if labeled forms of antibody or antigen were allowed to bind competitively to the respective solid phase during the first incubation step. If labeled forms of antibody or antigen were not present during the first incubation step, they will be added during a second incubation step, and then allowed to bind non-competitively to the respective signal probes 210 and 216. At completion of the assay, unbound analyte 200 or 202 are separated from the solid phase bound analyte antigen 200 or antibody 202 and quantified based on the extent of bound labeled signal antibody 210 or signal antigen 214.

With reference now to FIG. 23C, there is depicted an antibody-analyte-antibody sandwich assay wherein a capture antibody 204 is bound to the solid support 206 and analyte antigen 200 is allowed to bind to the capture antibody 204. The amount of bound analyte 200 is then determined through binding and measurement of labeled signal antibody 210. Conversely, an analyte-antibody-analyte sandwich assay has a solid phase 206 having the analyte 200, bound thereto, which captures bridging antibody 212. The analyte 200, in turn becomes enumerated through the binding of suitable labeled forms of the analyte 200 or signal antigen 214 utilizing, for example, the well known bivalency of Immunoglobulin G (IgG) and IgD, as depicted in FIG. 23D.

Quantification of target ligand or antigen molecules is most efficiently done by the two-antibody sandwich assay represented by FIG. 23C. The capture antibody 204 is immobilized on the solid support 206 and the signal antibody 210 is tagged or labeled with a suitable reporter 208. The recognition of the same antigen by two different binding antibodies, namely the solid phase capture antibody 204 and the reporter linked signal or enumerating antibody 210, contributes to the exquisite specificity of the assay. The capture antibody 204 identifies a first epitope on the surface of the ligand molecule while reporter antibody recognizes a second epitope at a different location on the surface of the same analyte or ligand molecule 200. The signal generated by the capture antibody-antigen-signal antibody complex is proportional to the amount of the bridging analyte (antigen) 200 present in the sample. The concentration of antigen in the analyzed specimen can then be determined through comparison with the signal generated by known quantity of pure antigen. An example of an assay based on this technique using radioiodine I-125 labeled antibody for detection of the antigen associated with serum hepatitis is optical bio-disclosed in U.S. Pat. No. 3,867,517. Alternatively, two signal antibodies may be preferably used wherein a primary unlabelled signal antibody is utilized to bind to the analyte that is bound to the solid phase through the capture antibody. After binding of the primary antibody a secondary labeled signal antibody, having specific affinity to the primary signal antibody is introduced and allowed to bind to the primary signal antibody. This essentially amplifies the signal coming from the reporter since multiple secondary antibodies may bind to the same primary antibody thus increasing the sensitivity of the assay.

Detection or quantification of antibody or any immunoglobulin is most frequently done by a solid phase immobilized antigen test device, as shown in FIG. 23D. The analyte or target antibody 212 is allowed to bind to the capture antigen 200 creating an immobilized antigen-antibody complex. A labeled form of an anti-immunoglobulin antibody or other immunoglobulin specific binding antibody (signal antigen) 214, is then applied to the immobilized antigen-antibody complex which enumerates the analyte antibody 212 through binding of the signal antigen 214 to a site other than the epitope binding site of the target antibody 212. Detection of the signal generated directly or indirectly by the tagged reporter or signal antigen 214 becomes a measure for the presence and quantity of the analyte antibody 212 when comparison with a known reference material for the immunoglobulin is established.

More recently, antibodies are determined by antigen sandwich, dubbed "inverse sandwich" immunoassays. This assay makes use of the presence of two equal epitope binding sites on each immunoglobulin G (IgG) molecule, thus allowing for a simultaneous binding of the analyte antibody 212 to two separate antigens, solid phase bound antigen 200 and labeled form of the same antigen 214 having tag 208, both having substantially identical epitopes. Lateral flow antigen sandwich immunoassays have one antigen/hapten immobilized to a solid phase, most frequently a nitrocellulose or nylon membrane, and the second antigen, carrying the same epitope as the solid phase bound antigen, labeled with enzyme, radioisotope, dye, or other signal generating substance. Antibody specific to the epitope represented by both antigens can than be specifically detected in a single step assay procedure.

It is thus the aim of this invention to transfer all antibody and antigen binding assays specifically including cell related assays, and probe assays from micro-titer plate, test tube, gel, or glass slide format to the optical analysis optical bio-disc format. Furthermore, multiple and lengthy incubation steps, washing steps, reagent addition steps and similar processing steps are eliminated and reduced to a one step assay procedure. The potential for optical bio-discrete patterned deposition and identification of addressable capture zones or microarrays 147 with imprinted single or multiple analyte specific reaction, target, or capture zones 140 may also be implemented on the optical bio-disc 110 as illustrated in FIG. 15.

Antibodies or analyte tagged with fluorescent dyes or linked to micro-particles, preferably fluorescent micro-particles with excitation wavelength covering the energy range of, for example, blue, green, and red laser, may be employed in the present invention.

FIGS. 24A, 24B, and 24C are pictorial representations of a cross-linking system used in an embodiment of the present invention. It should be understood that a cross-linking system involves one or more cross-linking agents, or conjugates, to cross-link one or more macromolecular moieties to another. A cross-link may be a covalent or non-covalent interaction between two macromolecular moieties, usually formed when two macromolecular free radicals combine. Chemical modifications or conjugation processes to achieve cross-links involve the reaction of one functional group with another, resulting in the formation of a bond. The creation of bioconjugate reagents with reactive or selectively reactive functional groups forms the basis for simple and reproducible cross-linking or tagging of target molecules ("*Bioconjugate Techniques,*" Greg T. Hermanson, Academic Press, San Diego, Calif., (1996)).

Cross-linking agents include, but are not limited to homobifunctional linkers, heterobifunctional linkers, and zero-length cross-linkers. Homobifunctional linkers are linkers with two reactive sites of the same functionality, such as glutaraldehyde. These reagents could tie one protein to another by covalently reacting with the same common groups on both molecules. Heterobifunctional conjugation reagents contain two different reactive groups that can couple to two different functional targets on proteins and other macromolecules. For example, one part of a cross-linker may contain an amine-reactive group, while another portion may consist of a sulfhydryl-reactive group. The result is the ability to direct the cross-linking reaction to selected parts of target molecules, thus garnering better control over the conjugation process. Zero-length cross-linkers mediate the conjugation of two molecules by forming a bond containing no additional atoms. Thus, one atom of a molecule is covalently attached to an atom of a second molecule with no intervening linker or spacer. One of ordinary skill in the art would refer to "*Bioconjugate Techniques,*" Greg T. Hermanson, Academic Press, San Diego, Calif., (1996), for a detailed description of cross-linking agents.

In the present invention, cross-linking agents are bound to the surface of an optical bio-disc to immobilize capture agents or probes within the target zones. A preferred cross-linking or affinity binding system is the heterobifunctional group consisting of biotin-streptavidin, i.e. biotinylated capture agents bound to an avidin-coupled substrate.

With specific reference now to FIG. 24A, there is shown a pictorial representation of streptavidin 218. Without limitation, streptavidin includes avidin, streptavidin, Neutravidin, and modifications, thereof. As shown, the protein comprises four subunits, each of which contains one binding site for biotin (Hermanson). Streptavidin 218 can be coupled to plastics such as polystyrene, polycarbonate or nitrocellulose by various chemistries. Ideally, streptavidin 218 is attached to the active layer 144 (FIGS. 4 and 9) of the optical bio-disc, binding essentially irreversibly to biotinylated capture agents or sensing elements (e.g. antibodies).

Turning to FIG. 24B, there is depicted a pictorial representation of biotin 220. Biotin (or vitamin H) is a naturally occurring growth factor present in small amounts within every cell. Biotin's interaction with the proteins: avidin and streptavidin is among the strongest non-covalent affinities known. A biotin molecule 220 may be attached directly to a protein via its valeric acid side chain or derivitized with other organic components to create spacer arms and various reactive groups. Amines, carboxylates, sulfhydryls, and carbohydrate groups can be specifically targeted for biotinylation through the appropriate choice of biotin derivative (Hermanson). FIG. 24C is a pictorial representation of the cross-linking system consisting of biotin 220 interacting with streptavidin 218.

Implementations of the embodiments of the invention utilize capture agents to perform the assays described herein. It should be understood that a capture agent refers to any macromolecule for detecting an analyte. The capture agents of the invention include macromolecules preferentially selective, or having a selective binding affinity, for an analyte of interest. Capture agents include, but are not limited to, synthetic or biologically produced nucleic acid and synthetic or biologically produced proteins. Examples of capture agents that can be employed by this invention, include, but are not restricted to, deoxyribonucleic acid (DNA), ribonucleic acid (RNA), oligonucleotides, polymerase chain reaction products, or a combination of these nucleotides (chimera), antibodies (monoclonal or polyclonal), cell membrane receptors, and anti-sera reactive with specific antigenic determinants (such as on viruses, cells, or other materials), drugs, peptides, co-factors, lectins, polysaccharides, cells, cellular membranes, and organelles. Preferably, capture agents of the invention are antibodies and/or antigens.

Antibodies include, but are not limited to polyclonal, monoclonal, and recombinantly created antibodies. Antibodies of the invention can be produced in vivo or in vitro. Methods for the production of antibodies are well known to those skilled in the art. For example, see Antibody Production: Essential Techniques, Peter Delves (Ed.), John Wiley & Son Ltd, ISBN: 0471970107 (1997), which is incorporated herein in its entirely by reference. Alternatively, antibodies may be obtained from commercial sources, e.g., Research Diagnostics Inc., Pleasant Hill Road, Flanders, N.J. 07836. Antibodies of the invention are not meant to be limited to antibodies of any one particular species; for example, antibodies of humans, mice, rats, and goats are all contemplated by the invention. Preferably, primary capture antibodies of the invention are anti-human produced in mice, and secondary capture antibodies of the invention are anti-mouse produced in goats.

The term "antibody" is also inclusive of any class or subclass of antibodies, as any or all antibody types may be used to bind to antigens including cell surface antigens. The use of antibodies in the art of medical diagnostics is well known to those skilled in the art. For example, see Diagnostic and Therapeutic Antibodies (Methods in Molecular Medicine), Andrew J. T. George and Catherine E. Urch (Eds.), Humana Press; ISBN: 0896037983 (2000) and Antibodies in Diagnosis and Therapy: Technologies, Mechanisms and Clinical Data (Studies in Chemistry Series), Siegfried Matzku and Rolf A. Stahel (Eds.), Harwood Academic Pub.; ISBN: 9057023105 (1999), which are incorporated herein in their entirety by reference.

In at least some embodiments of the invention, a plurality of capture agents is used to detect analytes of interest. FIG. 24D is a pictorial representation of the IgG class of antibodies used in the methods of the invention as a capture antibody 204. It should be understood that capture antibodies of the current invention include, but are not limited to, agents having an affinity for other capture agents (primary capture agents), which have an affinity for the analyte of interest. FIG. 24E shows a capture antibody 204 bound or conjugated to a biotin molecule 220.

Referring now to FIG. 24F, there is shown a pictorial representation of a signal antibody 210. It should be understood that both the capture antibody 204 and the signal antibody 210 of the invention have selective affinity for the analyte of interest. Preferably, the capture agent is an antibody having an affinity for human chorionic gonadotropin (HCG) or any analyte of interest present in bodily fluids. FIG. 24G shows a signal antibody 210 bound or conjugated to a biotin molecule 220.

Referring next to FIGS. 25A and 25B, there are depicted pictorial representations of two embodiments for binding capture antibodies 204 on the active layer 144 in a first implementation of the invention. FIG. 25A shows binding of a biotinylated capture antibody 204 (FIG. 24E) to streptavidin 218 which is bound to the active layer 144. Thus the capture antibody 204 is immobilized on the active layer 144 of the optical bio-disc 110 (FIGS. 4 and 9) by the affinity binding agent streptavidin 218. FIG. 25B shows an alternative embodiment to FIG. 25A where a streptavidin conjugated capture antibody 204 is bound to the active layer 144 by biotin 220. FIGS. 23B and 23C, above, show yet another embodiment of the same implementation of the invention without a cross-linking system. In this embodiment, capture antibodies 204 are immobilized directly on the active layer 144, metal layers 143 or 142, or substrate 120 of the optical bio-disc 110.

The optical bio-disc device 110 builds upon a polymer optical bio-disc with nanometer thick layer of a reflective metal 142 or 143, integrated information for reading the optical bio-disc by means of a laser being part of an optical reader and a biochemical layer. It is the function of the biochemical layer of the optical bio-disc to interact with substances of the analyzed specimen, in such a way, that only a specific analyte is selected, becomes bound and quantified. This aspect of the present invention is illustrated in FIG. 26 depicting an enlarged detailed partial cross sectional view of a capture or target zone 140 showing the substrate 120, and metal layer 142 or 143 as implemented respectively on the reflective or transmissive formats of the optical bio-disc 110 of the present invention. FIG. 26 also shows interlayers or the active layer 144 capture agent 204, analyte 200, signal agent 210, and the reporter bead 211 of the present optical bio-disc 110. The bead 211 may be a microsphere or nanosphere that is optionally fluorescent labeled (fluospheres), phosphorescent, luminecent, or chemiluminescent. The bead 211 may also carry different chemical functionalities including, for example, carboxyl, amino, aldehyde, and hydrazine functional groups. These functional groups may facilitate binding of the signal agent. FIG. 26 illustrates the capture agent 204 attached to chemical interlayers 144 on the metal layer 142 or 143. In this embodiment, the capture agent 204 binds onto the interlayer 144 through various chemical processes described below in detail. Thiol or amine active groups may be covalently bound to the capture agent 204 to thereby produce a modified capture agent. The modified capture agent may then be directly bound through the attached active groups by covalent dative binding directly to the metal surface 142 or 143. If capture agent is a protein, direct binding of the capture agent to the gold surface may carried out through dative binding of exposed cysteine and methionine residues on the protein without the need for thiol or amine modification. The bond between the capture agent 204 and the active or inter layer 144 is sufficient so that the capture agent 204 remains attached to the active layer 144 within the target zone 140, when the optical bio-disc 110 is rotated. FIG. 26 also depicts the target agent or analyte 200 bound to the capture agent 204. A reporter 211 bound to the analyte through a signal agent 210 is also shown.

Referring next to FIGS. 27A–27G, there is illustrated a method according to the present invention for detecting or determining the presence of target antigen 200 in a sample, in conjunction with the optical bio-disc 110 according to the present invention. As shown in FIGS. 27A–27G and optical bio-discussed above in conjunction with FIGS. 2, 5, and 10, the optical bio-disc 110 includes the cap portion 116, the adhesive member 118 and the substrate 120. The optical bio-disc format may be either the reflective optical bio-disc format or the transmissive optical bio-disc format with varying elements to each respective cap portion 116 and substrate 120 as described in conjunction with FIGS. 4, 9, 14, and 15, above. Although the optical bio-disc composition between the different optical bio-disc formats may vary, the bio-chemical interactions remain the same.

Figure 27A:
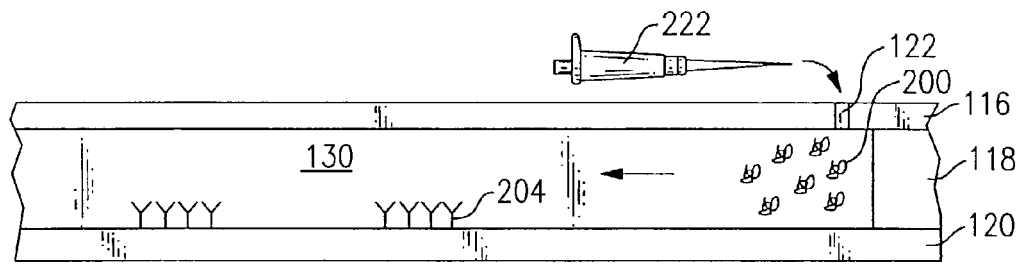
Figure 27B:
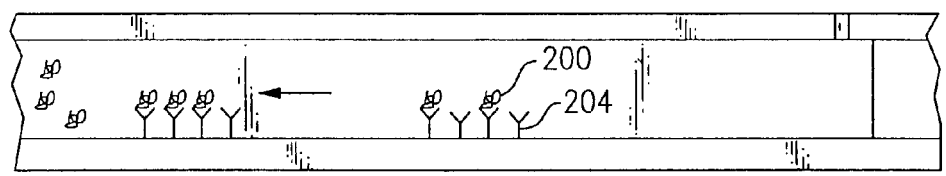
Figure 27C:
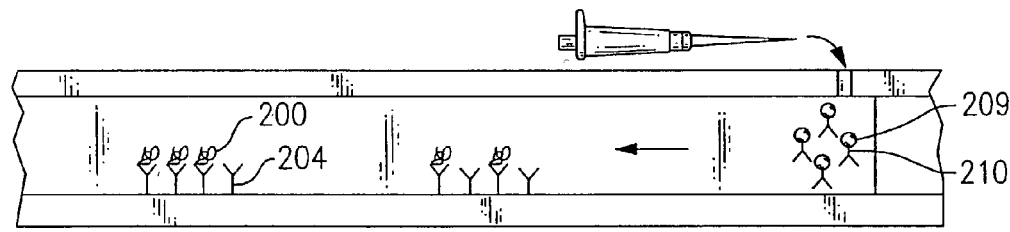
Figure 27D:
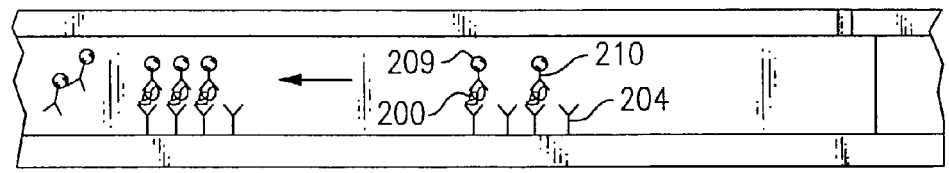
Figure 27E:
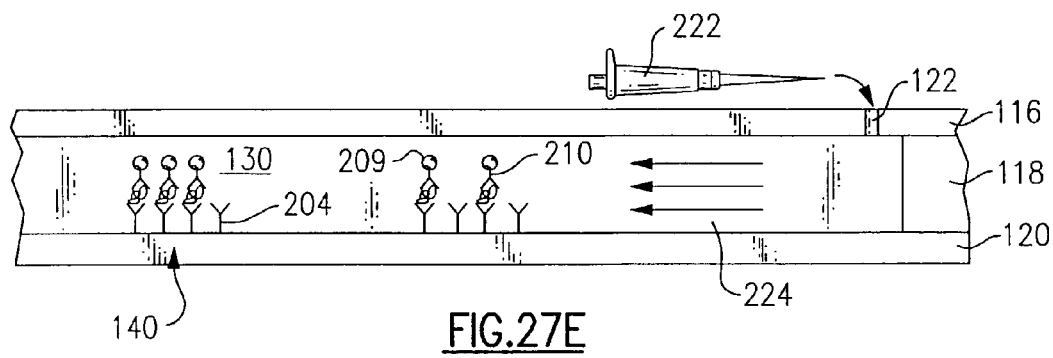
Figure 27F:
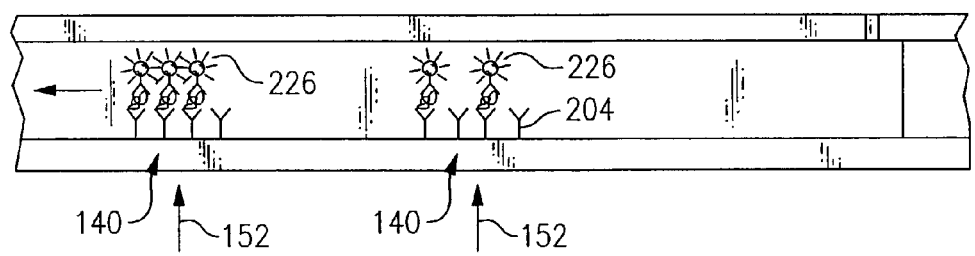
Figure 27G:
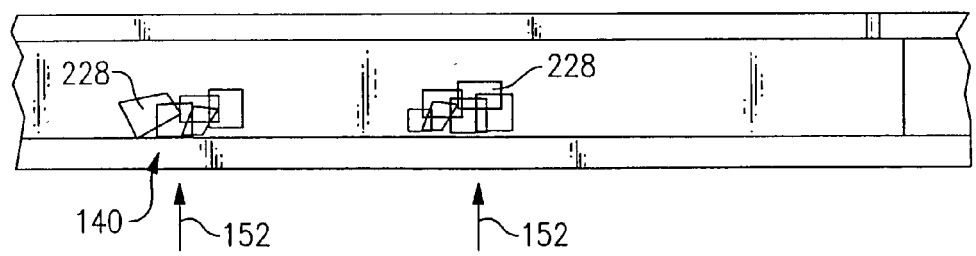

Referring specifically to FIG. 27A, a pipette 222 is loaded with a test sample with or without the target agent 200. The test sample is injected or deposited into the flow channel 130 through inlet or injection port 122. As the flow channel 130 is further filled with test sample, the target agent 200 begins to flow or move down the flow channel 130 as illustrated in FIGS. 27A and 27B. When the analyte of interest is present in the test sample, the analyte or target agent 200 binds specifically to the capture antibody 204 as shown in FIG. 27B. In this manner, the target agent 200 is retained within the target zone 140. Binding may be further facilitated by heating the optical bio-disc or localized heating of the flow channel. After binding, the flow channel 130 may be washed to clear the target zone 140 of any unattached target agents in the sample. After removing the unattached target agents in the sample, signal agents, probes, or antibodies 210 conjugated with enzymes 209 are introduced in the flow channel 130, FIG. 27C. As the flow channel 130 is filled with signal antibodies 210, the signal antibodies 210 begin to flow or move down the flow channel 130 as illustrated in FIGS. 27C and 27D. When the signal antibodies comes into close proximity with the target 200 bound in the target zone 140 by the capture probe 204, the signal antibodies 210 bind specifically to the target 200 as illustrated in FIG. 27D. After the signal agent binding step, the flow channel 130 may be washed to clear the target zone 140 of any unattached signal probe 210. Upon removal of unattached signal probe 210, enzyme-reactive substrates 224 are then introduced in the channel as shown in FIG. 27E. As the flow channel 130 is filled with enzyme substrate 224, the enzyme substrate 224 begin to flow or move down the flow channel 130 as illustrated in FIGS. 27E. When the substrate comes in contact with the enzyme 209 on the signal antibody 210 an enzyme-substrate reaction 226 occurs which results in the production of signal agents as shown in FIG. 27F. The signal agent may be color production, fluorescence, or luminophore production. The signal agent may also be precipitate 228 formation as illustrated in FIG. 27G. The incident or interrogation beam 152 may then be scanned through the target zone 140 to determine the presence of signal agents as illustrated in FIGS. 27F and 27G. In the event no target 200 is present in the test sample, no enzyme substrate reaction 226 will occur and the signal agents will not be present. In this case, when the interrogation beam 152 is directed into the target zone 140, a zero or baseline reading will result thereby indicating that no target 200 was present in the sample.

With reference now to FIGS. 28A–28D, there is shown another method according to the present invention for detecting or determining the presence of target antigen 200 in a sample in conjunction with the optical bio-disc 110 according to the present invention. As shown in FIGS. 28A–28D and optical bio-discussed above in conjunction with FIGS. 2, 5, and 10, the optical bio-disc 110 includes the cap portion 116, the adhesive member 118 and the substrate 120. The optical bio-disc format may be either the reflective optical bio-disc format or the transmissive optical bio-disc format with varying elements to each respective cap portion 116 and substrate 120 as described in conjunction with FIGS. 4, 9, 14, and 15, above. Although the optical bio-disc composition between the different optical bio-disc formats may vary, the biochemical interactions remain the same.

Figure 28A:
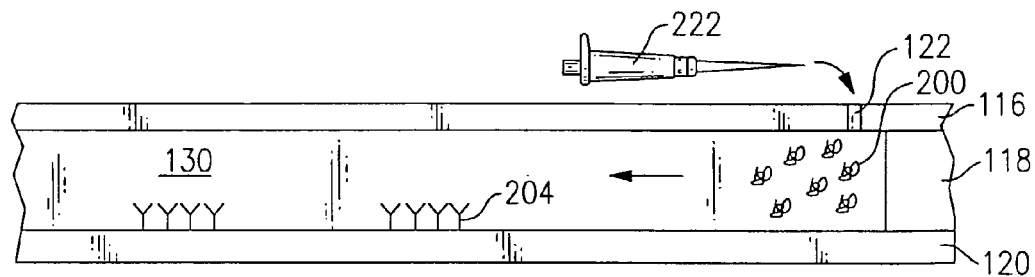
Figure 28B:
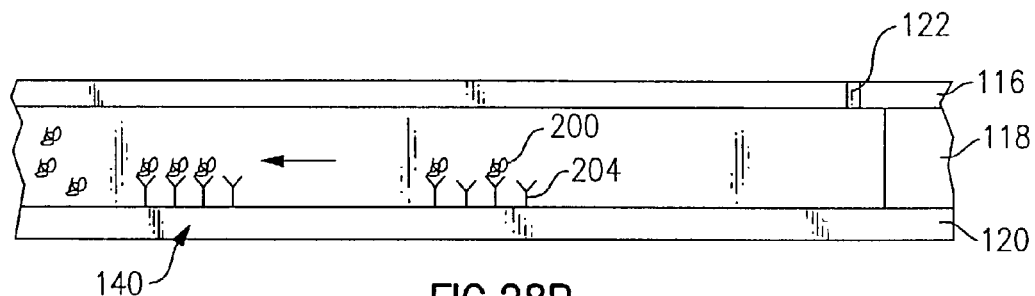
Figure 28C:
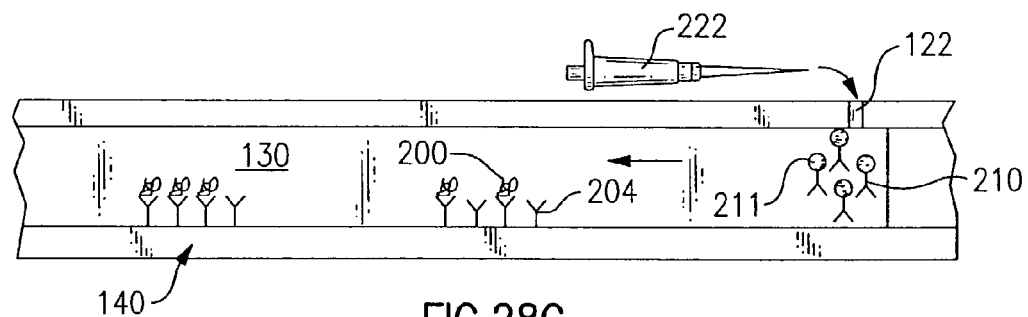
Figure 28D:
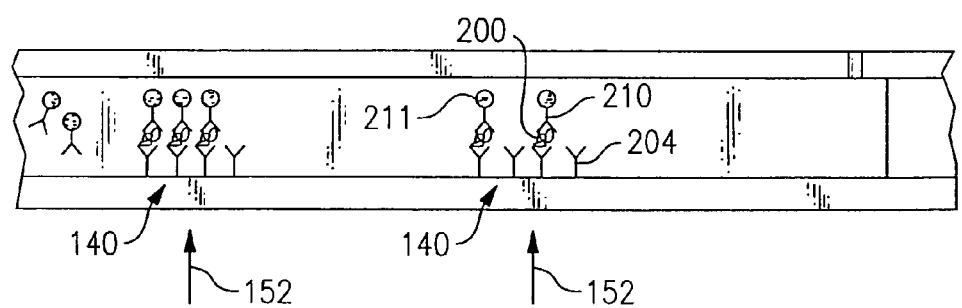

Specifically, FIG. 28A shows a pipette 222 loaded with a test sample with or without the target agent 200. The test sample is injected or deposited into the flow channel 130 through inlet or injection port 122. As the flow channel 130 is further filled with test sample, the target agent 200 begin to flow or move down the flow channel 130 as illustrated in FIGS. 28A and 28B. When the analyte of interest of is present in the test sample, the analyte or target agent 200 binds specifically to the capture antibody 204 as shown in FIG. 28B. In this manner, the target agent 200 is retained within the target zone 140. Binding may be further facilitated by heating the optical bio-disc or localized heating of the flow channel. After binding, the flow channel 130 may be washed to clear the target zone 140 of any unattached target agents in the sample. After removing the unattached target agents in the sample, signal agents, probes, or antibodies 210 conjugated with microspheres or beads 211 are introduced in the flow channel 130, FIG. 28C. As the flow channel 130 is filled with signal antibodies 210, the signal antibodies 210 begin to flow or move down the flow channel 130 as illustrated in FIGS. 28C and 28D. When the signal antibodies 210 comes into close proximity with the target 200 bound in the target zone 140 with the capture probe 204, the signal antibodies 210 bind specifically to the target 200 as illustrated in FIG. 28D. After the signal agent binding step, the flow channel 130 may be washed or spun to clear the target zone 140 of any unattached signal probe 210. The incident or interrogation beam 152 may then be scanned through the target zone 140 to determine the presence of beads 211 as illustrated in FIG. 28D. In the event no target 200 is present in the test sample, no beads 211 will be detected and the signal antibodies will not be present. In this case, when the interrogation beam 152 is directed into the target zone 140, a zero or baseline reading will result thereby indicating that no target 200 was present in the sample. Alternatively, the signal antibodies may be conjugated with biotin or streptavidin and additional steps of washing and respectively binding streptavidin or biotin coated beads 211 to the signal antibodies 210 bound to the target 200 in the target zone 140 may be implemented.

One preferred method for performing an optical bio-disc based binding assay is a single step assay wherein all binding washing, separation, and enumeration steps, of an immunochemical assay for example, is replaced by one single sample binding step followed by analysis of the capture zones. In this method, all the binding and reporter reagents are pre-loaded into the optical bio-disc and in use only the sample is added, the sample incubated to allow sufficient time for binding of the analyte in the sample to both capture and signal agents. After incubation, the excess sample reagent and any unbound signal agents and reporters are removed from the flow channel or fluidic channel by rotating the optical bio-disc so that the unbound reagent move from the flow channel into the waste reservoir of the optical bio-disc 110, as illustrated above in FIGS. 10–15, for example. If the reporters used are fluorescent, then the bound reporters may be quantified using a fluorescent type reader or a fluorescent scanner as described below in Example 5.

Methods for Attaching Capture Probe onto Solid Support

From the many known analytical and biochemical methods, the most widely used procedure for quantitative and qualitative analysis of complex samples are protein binding assays based on selective affinity of the binding reagent and the analyte as described above in conjunction with FIGS. 23–28. Several methods may be used to form functionally active biochemical layer or active layer 144 on the polycarbonate (PC) or gold surface of the optical bio-disc substrate 120. Passive adsorption is one preferred method for achieving the linkage of a bio-chemical, chemical, binding reagent, or capture agent to the polymer or metal surface of the optical bio-disc substrate 120. Large bio-molecules containing pockets of hydrophobic amino acids, carbohydrates, and similar components are easily linked to a non-polar polymer surface through passive adsorption. The hydrophobic forces exhibited by the polymer substrate and the bio-molecule or capture agent, as well as the electrostatic interaction between the substrate and the capture agent, result in the formation of a stable linkage. The pH, salt concentration, and presence of competing substances will, among other factors, determine the extent to which various capture agents link non-covalently to the plain surface of the polymer or the metal covered polymer surface of the optical bio-disc 110. If the capture agent is a protein, the pH of the coating buffer containing the capture agents affects the binding of the capture agent onto the polymer substrate or metal layer. A pH of the coating buffer solution close to the isoelectric point of the capture agent will increase the hydrophobicity of the protein thus leading to a stronger interaction of the protein with the substrate resulting in stronger bonding and most likely also to higher density of immobilized capture agent.

Alternatively, thiolated capture agents may be immobilized onto the gold or metallic surface through dative binding of thiol active groups on the capture agents. In one preferred embodiment of the present invention, the capture agents are proteins, these capture agents may be directly bound to the gold surface covalently by dative binding to form metalorganic bonds through cysteine or methionine residues of the capture agent or binding protein. The dative binding of the thiol or methionine active groups may be facilitated by a mild reducing agent such as sodium cyanoborohydride ($NaCNBH_3$). In yet another embodiment of the present invention, thiolated forms of: biotin, streptavidin, avidin, Neutravidin, and BSA-biotin may be initially bound to the gold surface by dative binding, either directly through cysteine and methionine residues on the surface of these proteins or through attached thiol active groups on thiolated proteins. Capture agents conjugated with an appropriate binding pair including biotin, streptavidin, Neutravidin, and avidin are then introduced onto the capture zone and allowed to bind to the active layer having the respective affinity agents. In still another embodiment, streptavidin or biotin may be used as a bridging agent to bind respectively, a biotinylated or streptavidinated, active layer to its respective streptavidinated or biotinylated capture agent.

Passive adsorption of the capture agents may not work for a number of bio-polymers that do not interact passively with the chemically inert surface of the polymer substrate or the metal covered polymer substrate. This is because there may be a lack of sites for non-covalent interaction. Proteins of low molecular weight, polypeptides, and molecules with predominantly ionic character, for example, do not link to polymer surfaces due to lack of, or the presence of only very weak, hydrophobic or electrostatic interaction.

Another critical aspect of immobilizing binding proteins or capture agents onto a solid support is the retention of functional activity of bound protein or capture agent. Frequently, the capture agents loose their biochemical properties due to denaturation in the process of immobilization involving structural reorganization followed by conformational changes and accompanying changes of functionally active sites. Enzymes, receptors, lectins, and antibodies are examples of such bio-polymers, binding proteins, or capture agents.

Situations where the lack of passive interaction with the support polymer substrate or the loss of functional activity due to the immobilization process, necessitate another approach. The approach taken in these cases leads to the functionalization of the chemically inert surface of the substrate upon which the immobilization of the biochemical reagent is intended. Functionalization is a process by which the substrate or metal surface is modified by attaching specific molecules or polymers with functional groups to the surface. The functional groups are then used to bind recognition molecules such as binding proteins, capture antibodies, receptors, and other similar assay components. Structural changes of the binding protein at regions of the molecule known not to harbor vital biochemical function will augment the contribution derived from the modified substrate or metal surface.

Surfaces of polymeric materials have been modified previously. See for instance Braybrook et al., Prog. Polym. Sci. 15:715–734, 1990. Most of the modification procedures known in the art involve sequential treatment of surfaces with chemical reagents. Examples include sulfonation of polystyrene, Gibson et al., Macromolecules 13:34, 1980; base hydrolysis of polyimide, Lee et al., Macromolecules 23:2097, 1990; and base treatment of polyvinylidene fluoride, Dias et al., Macromolecules 17:2529, 1984. Another conventional method for modifying polymer surfaces includes exposing the surface of the hydrocarbon such as polyethylene with nitrene or carbene intermediates generated in a gas phase (Breslow in "Azides and Nitrenes", chapter 10, Academic Press, New York, 1984). Perfluorophenyl azides (PFPAs) have been shown to be efficient in the insertion in CH bonds over their non-fluorinated analogues (Keana et al., Fluorine Chem. 43:151, 1989). Recently, bis-(PFPA)s have been shown to be efficient cross-linking agents for Polystyrene (Cai et al., Chem. Mater. 2:631, 1990).

Chemical modification of the inert polymer substrate surface is efficiently done through grafting procedures that allow the deposition of a thin interphase layer, active layer, or interlayer on the substrate of the optical bio-disc 110. Ideally, the interphase layer should make a stable linkage of the grafted material to the substrate surface and contain a spacer molecule ending in a functional group or variety of chemically different functional groups. This allows the selection of specific surface chemistries for efficient covalent immobilization of a variety of capture agents with different demand for spatial orientation, side directed attachment within the structure of the binding protein. The introduction of spacer molecules, especially hydrophilic spacers as part of the graft, contributes significantly to the flexibility and accessibility of the immobilized capture agents. By placing a spacer layer between the solid phase of the substrate modified or grafted with different functional groups and the binding protein, a potentially denaturing effect of the direct contact of the protein with the functional groups is eliminated.

Selective, binding protein tailored chemistries permit the retention of functional activity of the immobilized capture molecule or agent. As a consequence, one can expect chemistries on the solid phase/liquid phase interphase of the capture agent-analyte to approach those of the liquid phase. This is especially true with the increased access of the analyte as processed on the optical bio-disc. In addition, reaction conditions of the liquid phase can be replicated on the optical bio-disc.

A potential benefit of a graft modified substrate surface is the "normalization" of the surface with respect to the uniformity in density of the immobilized binding protein. Also, bonds between capture reagent and graft mediated polymer support become more uniform. This results in holding each molecule of binding protein with the same bond energy. This aspect becomes of paramount importance for any quantitative assay especially on the micrometer design of protein and DNA microarrays.

Experimental Details

While this invention has been described in detail with reference to the drawing figures, certain examples and further details of the invention are presented below. These examples are provided by way of illustration, and are not intended to be limiting of the present invention.

EXAMPLE 1

Direct Binding of Capture Antibodies on the Metal Layer

A 2 mg amount of affinity purified anti-HCG-alpha capture antibody (Biocheck, Burlingame, Calif.) was dissolved in 2% glycerol in PBS, pH 7.4 to obtain a 100 ug/ml stock solution. A pin stamper was used to directly apply multiple spots of 0.2–0.3 ul of the capture antibody stock solution on the gold metal layer (150 Angstroms thick) of the transmissive optical bio-disc substrate with two concentric peripheral reservoirs as shown above in FIG. 11A. The optical bio-disc was then incubated in a humid environment using a humidity chamber at room temperature overnight. After incubation, the optical bio-disc was washed with a gentle stream of deionized water to remove excess unbound capture antibodies and spun dried at 1000–1500 rpm. Three absorber pads, with dimensions of the peripheral reservoir are then placed in the outer peripheral reservoir, as shown above in FIG. 13. The cap portion having attached thereto the adhesive layer, having fluidic circuits formed therein, is then applied onto the substrate. After the optical bio-disc is fully assembled, the fluidic channels are then filled with blocking buffer (10 ul/channel) containing 1% BSA, 1% Sucrose, 0.1% Tween-20 in PBS, pH 7.4. The optical bio-disc is incubated for 2 hours to allow the blocking agents sufficient time to bind to unoccupied sites on the capture zone, cover optical bio-disc, and substrate to prevent or minimize non-specific binding of reporter agents onto unwanted sites. After blocking, the excess blocking buffer is aspirated and the channels are filled with deionized water (10 ul/channel) to remove excess salt from the blocking buffer. The water is then aspirated and the optical bio-disc is kept at 4 degrees Celsius prior to use.

EXAMPLE 2

Purification of Microspheres

Microspheres may be purified using dialysis or centrifugation. With centrifugation, bead suspensions are centrifuged at a speed required to precipitate the particles. The speed is determined empirically and depends on the mass of the beads and the density of the buffer containing the beads (e.g., 0.2 um Fluospheres (Molecular Probes) in PBS or conjugation buffer may be centrifuged at 6000 rpm for 30 mins and 0.5 um Fluospheres (Molecular Probes) in PBS may be centrifuged at 14000 rpm for 20 mins.). After the initial centrifugation of the bead suspension, the supernantant is optical bio-discarded and the beads are resuspended in a conjugation buffer. The conjugation buffer is preferably a low ionic strength sodium phosphate buffer (PBS) having a pH slightly above the isoelectric point of the signal agent to be conjugated to the microspheres. The centrifugation, aspiration, and resuspension steps are repeated three times and the final pellet of beads is resuspended in conjugation buffer to obtain a suspension containing 10 mg/ml microspheres. The purified bead suspension is then stored at 4 degrees Celsius and sonicated for 30 seconds prior to use.

EXAMPLE 3

Passive Adsorption of Signal Antibodies to 0.2 um Fluospheres 5.0 mg of purified and sonicated 0.2 um polystyrene carboxylate Fluospheres (Molecular Probes, Eugene, Oreg.), prepared as described in Example 2, were dispensed into 250 ul of 20 mM Sodium Phosphate buffer, pH 7.2 in a 1.7 ml Costar centrifuge tube. The beads were mixed in a vortex mixer and an additional 250 ul of Sodium Phosphate buffer was then added to the bead suspension. Then 250 ug of anti-HCG-beta was added to the bead suspension and immediately mixed using a vortex mixer. The tube containing the bead suspension was then placed on a Dynal mixer and rotated to 40 hours at 4 degrees Celsius shielded from light. After incubation, the beads were spun at 6000 rpm for 15 mins, the supernatant was aspirated and the pellet was resuspended with 500 ul of 20 mM Sodium Phosphate buffer, pH 7.2, sonicated for 30 seconds. After the initial washing step, the beads were further washed 3 times with 500 ul of 20 mM Sodium Phosphate buffer, pH 7.2 by repeated aspiration and spin cycles of 6000 rpm for 30 mins. The final pellet was then reconstituted with 1.0 ml 20 mM Sodium Phosphate buffer, pH 7.2 to obtain a final microsphere concentration of 5.0 mg/ml. The anti-HCG-beta conjugated microspheres were then stored at 4 degree Celsius.

EXAMPLE 4

Conjugation of Anti-HCG-Beta to 0.5 um Fluospheres

A 400 ul bead suspension containing 4 mg of 0.5 um carboxylate polystyrene Fluospheres (Molecular Probes, Eugene, Oreg.) in PBS, prepared as described in Example 2, was dispensed into a 1.7 ml Costar centrifuge tube. Then 200 ug of anti-HCG-beta antibody in 15 mM potassium phosphate, 145 mM sodium chloride, pH 7.4 buffer was added to the bead suspension. The resulting antibody-bead suspension was then mixed using a Dynal rotator at room temperature for 4 hours. The suspension was then further incubated at 4 degrees Celsius without mixing for an additional 36 hours. After incubation, the beads were spun at 14000 rpm for 20 mins, the supernatant was aspirated and the pellet was resuspended with 500 ul of 20 mM Sodium Phosphate buffer, pH 7.2. After the initial washing step, the beads were further washed 3 times with 500 ul of 20 mM Sodium Phosphate buffer, pH 7.2. The final pellet was then reconstituted with 800 ul 20 mM Sodium Phosphate buffer, pH 7.2 containing 0.05% sodium azide. The anti-HCG-beta conjugated microspheres were then stored at 4 degree Celsius.

EXAMPLE 5

HCG Assay Using the Optical Bio-Disc

Materials:
1. Fully assembled optical bio-disc made according to Example 1;
2. HCG standard or unknown in 1% BSA PBS 7.4, 0.05% sodium azide;
3. Bead Conjugate Dilution Buffer (BCDB): 1% BSA, 0.1% Tween-20, and 0.05% sodium azide in PBS 7.4; and
Note: The BSA concentration may be 0.1–10%; sucrose may be replaced with other sugars including glucose, fructose, trehalose, or lactose at a concentration of 0.1–10%; Tween-20 may be replaced with other non-ionic detergents including Triton X-100 and Tween-80 at a concentration of 0.1–5%; and sodium azide concentration may range from 0.01 to 1%.
4. 0.2 um or 0.5 um Fluospheres conjugated with Anti-HCG-beta, respectively made according to either Example 3 or 4, washed and resuspended in BCDB.

Assay:
Various concentrations (0, 12.5, 25, 50, 250, and 500 mIU/ml) of HCG standard were mixed with an equal volume (10 ul) of 0.5 um Fluospheres conjugated with anti-HCG-beta in BCDB. Prior to use, the Fluospheres were washed and reconstituted in BCDB to obtain a bead concentration of 25 ug Fluospheres/ml of BCDB. The assay solutions were mixed and a 10 ul aliquot of each suspension was applied, using a pipette, through the inlet port into various channels in the optical bio-disc such as those shown and described in conjunction with FIGS. 10, 11A, 13, and 15. The optical bio-disc containing the assay solutions was incubated at room temperature for 30 minutes. After incubation, the unbound beads and HCG were removed by spinning the optical bio-disc at 2500 rpm for 6 minutes. This spin was enough to move all the liquid, containing unbound Fluospheres, out of the fluidic circuits to the inner and then to the outer peripheral circumferencial waste reservoir and into the absorber pads. After evacuating the fluidic circuits or channels, the amount of beads bound to the capture zones were quantified using a Molecular Dynamics Fluorescent Scanner model FluorImager 595. The results from this experiment are shown below in Table 2. The data presented below indicates that, for this particular experiment, the linear range of detection of HCG using the optical bio-disc is from 0 mIU/ml to 500 mIU/ml HCG when graphed in a semi-log format. The quantification of these beads may also be carried out using a fluorescent type optical bio-disc reader or the optical bio-disc reader as described above in conjunction with FIG. 16.

TABLE 2

Various concentrations of HCG Standards Quantified Using the Optical bio-disc of the Present invention (Data are in Relative Fluorescence Units.).

| HCG Concentration (mIU/ml) | 0 | 12.5 | 25 | 50 | 250 | 500 |
|---|---|---|---|---|---|---|
| Capture Zone | | | | | | |
| 1 | 10468 | 11675 | 16002 | 16042 | 20610 | 23583 |
| 2 | 9869 | 11549 | 16388 | 17409 | 22868 | 25793 |
| 3 | 9869 | 12770 | 15079 | 18298 | 24475 | 26131 |
| Average | 10069 | 11998 | 15823 | 17250 | 22651 | 25169 |
| SD | 282 | 548 | 549 | 928 | 1585 | 1130 |
| % RSD | 2.8 | 4.6 | 3.5 | 5.4 | 7.0 | 4.5 |
| Background Subtracted Data | 0 | 1930 | 5755 | 7181 | 12583 | 15101 |

CONCLUDING SUMMARY

All patents, provisional applications, patent applications, and other publications mentioned in this specification are incorporated herein in their entireties by reference.

While this invention has been described in detail with reference to a certain preferred embodiments, it should be appreciated that the present invention is not limited to those precise embodiments. Rather, in view of the present optical bio-disclosure that describes the current best mode for practicing the invention, many modifications and variations would present themselves to those of skill in the art without departing from the scope and spirit of this invention. The scope of the invention is, therefore, indicated by the following claims rather than by the foregoing description. All changes, modifications, and variations coming within the meaning and range of equivalency of the claims are to be considered within their scope.

Furthermore, those skilled in the art will recognize, or be able to ascertain, using no more than routine experimentation, many equivalents to the specific embodiments of the invention described herein. Such equivalents are also intended to be encompassed by the following claims.

The invention claimed is:
1. An optical bio-disc, comprising:
a substantially circular substrate having a center and an outer edge;
a metal layer in operable connection with the substrate;
a target zone disposed between the center and the outer edge;
an active layer formed on the surface of said metal layer;
at least one capture agent that binds to said active layer such that the capture agent is immobilized on said active layer within the target zone to thereby form a capture zone, wherein the capture zone is located within the optical bio-disc;
a first circumferential reservoir located near the outer edge of said substrate and extending around the periphery of said substrate; and
a second circumferential reservoir located adjacent to and extending around an interior edge of the first circumferential reservoir, wherein the second circumferential reservoir is in fluid communication with the first circumferential reservoir through at least one port which extends through a common barrier between the first and second circumferential reservoirs, and wherein said common barrier physically and circumferentially supports a cap member placed on said substrate.

2. The optical bio-disc according to claim 1 wherein the metal layer is selected from the group comprising aluminum, gold, silver, nickel, and reflective metal alloys.

3. The optical bio-disc according to claim 1 wherein the substrate includes encoded information, the encoded information being readable by a disc drive assembly to control rotation of the bio-disc.

4. The optical bio-disc according to claim 1 further comprising an enzyme, wherein the enzyme, when exposed to an enzyme substrate, produces a signal detectable by an incident beam of electromagnetic radiation.

5. The optical bio-disc according to claim 1 further comprising a flow channel in fluid communication with said capture zone and said first and second circumferential reservoirs, and an input site in fluid communication with said flow channel.

6. The optical bio-disc according to claim 1, further comprising a plurality of fluidic channels, each of said fluidic channels being in fluid communication with the first and second circumferential reservoirs.

7. The optical bio-disc according to claim 1 further comprising at least one absorber pad in fluid communication with the first circumferential reservoir.

8. The optical bio-disc according to claim 7, wherein the at least one absorber pad comprises a plurality of absorber pads positioned within the first circumferential reservoir at spaced locations so as to promote and maintain balance of the optical bio-disc when said bio-disc is in rotation.

9. The optical bio-disc according to claim 1, further comprising a drying agent or desiccant configured to absorb moisture so as to preserve functional activity of reagents deposited in the optical bio-disc.

10. The optical bio-disc according to claim 9, wherein the drying agent or desiccant is contained in an absorber pad located in fluid communication with the first circumferential reservoir.

11. An optical bio-disc, comprising:
a substantially circular substrate having a center and an outer edge;
a target zone disposed between the center and the outer edge;
at least one capture probe located within the target zone, wherein the capture probe is configured to immobilize a target agent from a sample within the target zone;
a first circumferential reservoir located near the outer edge of said substrate and extending around the periphery of said substrate; and
a second circumferential reservoir located adjacent to and extending around an interior edge of the first circumferential reservoir, wherein the second circumferential reservoir is in fluid communication with the first circumferential reservoir through at least one port which extends through a common barrier between the first and second circumferential reservoirs, and wherein said common barrier physically and circumferentially supports a cap member placed on said substrate.

12. The optical bio-disc according to claim 11, further comprising at least one absorber pad located in fluid communication with the first circumferential reservoir.

13. The optical bio-disc according to claim 12, wherein the absorber pad includes a drying agent or desiccant.

14. The optical bio-disc according to claim 12, wherein the at least one absorber pad comprises a plurality of absorber pads positioned within the first circumferential reservoir at spaced locations so as to promote and maintain balance of the optical bio-disc when said bio-disc is in rotation.

15. An optical bio-disc, comprising:
a substantially circular substrate having a center and an outer edge;
a metal layer in operable connection with the substrate;
a target zone disposed between the center and the outer edge of said substrate;
an active layer formed on the surface of said metal layer;
at least one capture agent that binds to said active layer such that the capture agent is immobilized on said active layer within the target zone to thereby form a capture zone, wherein the capture zone is located within the optical bio-disc, and wherein the active layer is formulated to immobilize a pellet formed by an enzyme reaction;
a first circumferential reservoir located near the outer edge of said substrate and extending around the periphery of said substrate;
a second circumferential reservoir located adjacent to and extending around an interior edge of the first circumferential reservoir, wherein the second circumferential reservoir is in fluid communication with the first circumferential reservoir through at least one port which extends through a common barrier between the first and second circumferential reservoirs wherein said common barrier physically and circumferentially supports a cap member placed on said substrate; and
a drying agent or desiccant in fluid communication with the first circumferential reservoir and configured to absorb moisture so as to preserve functional activity of reagents deposited in the optical bio-disc.

16. An optical bio-disc, comprising:
a substantially circular substrate having a center and an outer edge;
a metal layer in operable connection with the substrate;
a target zone disposed between the center and the outer edge;
an active layer formed on the surface of said metal layer;
a plurality of fluidic channels in fluid communication with the active layer;
at least one capture agent located in at least one of the fluidic channels, wherein said capture agent binds to said active layer such that the capture agent is immobilized on said active layer within the target zone to thereby form a capture zone, wherein the capture zone is located within the optical bio-disc;
a first circumferential reservoir located near the outer edge of said substrate and extending around the periphery of said substrate; and
a second circumferential reservoir located adjacent to and extending around an interior edge of the first circumferential reservoir, wherein the second circumferential reservoir is in fluid communication with the first circumferential reservoir through at least one port which extends through a common barrier between the first and second circumferential reservoirs, wherein said common barrier physically and circumferentially supports a cap member placed on said substrate, and wherein the second circumferential reservoir is in fluidic communication with said plurality of fluidic channels.

17. The optical bio-disc according to claim 16 further comprising at least one absorber pad in fluid communication with the first circumferential reservoir.

18. The optical bio-disc according to claim 17, wherein the at least one absorber pad comprises a plurality of absorber pads positioned within the first circumferential reservoir at spaced locations so as to promote and maintain balance of the optical bio-disc when said bio-disc is in rotation.

* * * * *